United States Patent
Kraemer et al.

(10) Patent No.: US 9,108,941 B2
(45) Date of Patent: Aug. 18, 2015

(54) GRISEOFULVIN ANALOGUES FOR THE TREATMENT OF CANCER BY INHIBITION OF CENTROSOMAL CLUSTERING

(75) Inventors: Alwin Kraemer, Karlsruhe (DE); Blanka Leber, Dossenheim (DE); Mads Clausen, Kopenhagen (DK); Thomas Larsen, Holte (DK); Mads Roennest, Virum (DK); Kasper Worm, Frederiksberg (DK)

(73) Assignee: DEUTSCHES KREBSFORSCHUNGSZENTRUM STIFTUNG DES OEFFENTLICHEN RECHTS, Heidelberg (DE)

( * ) Notice: Subject to any disclaimer, the term of this patent is extended or adjusted under 35 U.S.C. 154(b) by 290 days.

(21) Appl. No.: 13/141,231

(22) PCT Filed: Dec. 22, 2009

(86) PCT No.: PCT/EP2009/067761
§ 371 (c)(1),
(2), (4) Date: Oct. 25, 2011

(87) PCT Pub. No.: WO2010/072770
PCT Pub. Date: Jul. 1, 2010

(65) Prior Publication Data
US 2012/0035200 A1 Feb. 9, 2012

(30) Foreign Application Priority Data
Dec. 22, 2008 (EP) .................................. 08172542

(51) Int. Cl.
*C07D 307/94* (2006.01)
*A61K 31/343* (2006.01)
*C07D 405/12* (2006.01)
*C07D 407/12* (2006.01)

(52) U.S. Cl.
CPC ............ *C07D 307/94* (2013.01); *C07D 405/12* (2013.01); *C07D 407/12* (2013.01)

(58) Field of Classification Search
CPC ............................ C07D 307/94; A61K 31/343
See application file for complete search history.

(56) References Cited

U.S. PATENT DOCUMENTS

| 3,084,102 A | 4/1963 | Alfred |
| 3,102,123 A | 8/1963 | Clark et al. |
| 2005/0049207 A1 | 3/2005 | Kaufman |

FOREIGN PATENT DOCUMENTS

| EP | 2 008 652 A1 | 12/2008 |
| JP | 3-255081 | 11/1991 |
| WO | WO 97/05870 | * 2/1997 |

OTHER PUBLICATIONS

Crounse, "Antidermatophytic Properties of Griseofulvin Derivatives with Potential Systemic Insect-Repellent Activity," *J. Pharm. Sci.* 58(8):1022-1024, 1969.
Crowdy et al., "The Translocation of Antibiotics in Higher Plants. 4. Systemic Fungicidal Activity and Chemical Structure in Griseofulvin Relatives," *Biochem. J.* 72(2):241-249, 1959.
El-Nakeeb and Lampen, Formation of Complexes of Griseofluvin and Nucleic Acids of Fungi and its Relation to Griseofluvin Sensitivity, *Biochem. J.* 92(2):59P-60P, 1964.
Juvale et al., "Comparative 2D and 3D-QSAR of Antifungal Griseofulvin Analogues," *Indian J. Chem.* 45A(1):194-201, 2006.
Kovacic et al., "Are Reduction Potentials of Antifungal Agents Relevant to Activity?," *Pharm. Res.* 7(3):283-288, 1990.
Mir et al., "Correlation Between the In Vivo Effects of Some Griseofluvin Derivatives and Their In Vitro Interactions with Mammalian Microtubules," *FEBS Lett.* 88(2):259-263, 1978.
Oda, "Effects of 2'-Demethoxy-2'-Propoxygriseofulvin on Microtubule Distribution in Chinese Hamster V79 Cells," *J. Antibiotics* 59(2): 114-116, 2006.
Page and Staniforth, "Griseofulvin Analogues. Part V. Infrared Absorption," *J. Chem. Soc.* 1:1292-1303, 1962.
Rebacz et al., "Identification and Characterization of Centrosomal Cluster-Inhibitors as Novel Anti-Cancer Agents," Abstract P46, *Eur. J. Cancer Supplements* 4(6): 43-44, 2006.
Ronnest et al., "Synthesis and Structure-Activity Relationship of Griseofulvin Analogues as Inhibitors of Centrosomal Clustering in Cancer Cells," *J. Med. Chem.* 52(10):3342-3347, 2009.
Sato et al., "Structure-Activity Study of Griseofulvin and its Derivatives for the In Vitro Inhibition of Microtubule Protein Polymerization and the In Vitro Depolymerization of Microtubule Proteins," *Chemical Abstracts*, Accession No. 1981:526579, 1960.

(Continued)

*Primary Examiner* — James D Anderson
(74) *Attorney, Agent, or Firm* — Clark & Elbing LLP; Kristina Bieker-Brady

(57) ABSTRACT

The invention relates to compounds of the formula (I), where the symbols have the meaning given in the specification, for use in a method for treating cancer, to use of these compounds for the manufacture of a pharmaceutical composition for the treatment of cancer, and to methods of treatment for said diseases employing a compound of formula (I).

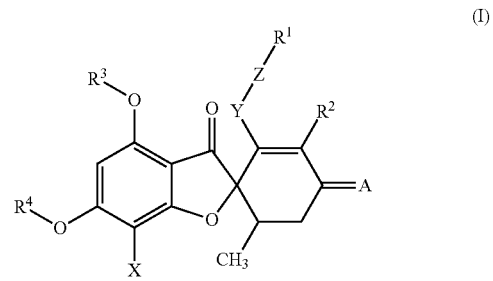

9 Claims, No Drawings

(56) References Cited

OTHER PUBLICATIONS

International Search Report for International Application No. PCT/EP2009/067761, completed Jul. 6, 2010, mailed Oct. 29, 2010 (4 pages).

International Preliminary Report on Patentability, including Notification of Transmittal and Written Opinion for International Application No. PCT/EP2009/067761, issued Jun. 29, 2011, mailed Jul. 7, 2011 (20 pages).

* cited by examiner

GRISEOFULVIN ANALOGUES FOR THE TREATMENT OF CANCER BY INHIBITION OF CENTROSOMAL CLUSTERING

CROSS REFERENCE TO RELATED APPLICATIONS

This application is a U.S. National Stage Application of International Application No. PCT/EP2009/067761, filed on Dec. 22, 2009, which claims priority to European Patent Application No. 08172542.6, filed on Dec. 22, 2008.

The present invention relates to uses of compounds having a structure as shown by formula (I) for the manufacture of a pharmaceutical composition for the treatment of cancer. The present invention encompasses methods of treatment for such diseases. The present invention is also directed to a part of the compounds disclosed in the present application as such.

A drawback of the current standard therapy for cancer using surgery, chemotherapy, high dosage chemotherapy including stem cell transplantation, radiation and $^{131}$I-MIBG therapy is the limited efficacy and selectivity accompanied by varying lethality rates, as the case may be. Moreover, serious side effects are regularly encountered.

Classical anti-cancer drugs use proliferation/cell division as a target, thereby killing all dividing cells without differentiating between cells belonging to the tumour that should be targeted and normal tissues. This lack of specificity causes most of the well-known and unavoidable side effects of classical chemotherapeutical agents.

There is a long-felt need to provide or identify compounds, which can be used for the treatment of cancer, the anti-tumoral mode of action of which shall not be based on the cytotoxic principles of traditional chemotherapy and which are selective for cancer cells only, not for normal, non-transformed cells of the body.

Griseofulvin (Chemical Abstract name: (2-5-trans)-7-chloro-2,4,6-trimethoxy-6-methylspiro-[benzofuran-2(3H), 1-(2)-cyclohexene]-3,4-dione; Chem. Abstr. Ser. No. 126-07-8; chemical structure see structure (II)) is a natural antibiotic produced by *Penicillium griseofulvum* as well as other microfungi and was isolated in 1938.

Griseofulvin is still commonly used in humans for the treatment of dermatomycoses in skin, hair, and nails caused by *Microsporum, Trichophyton*, and *Epidermophyton*. The mode of action on fungi is not fully understood, but it has been shown that it causes a reversible block of protein and nucleic acid synthesis and that its main effect on mitosis is apparently due to disorganization of the spindle microtubules. The daily dose for adults is 0.5 to 1 g (maximal 20 mg/kg bw.); in children it is 10 mg/kg bw. The treatment time depends on the type and localization of the infection, for hair infections 2 to 3 months, for onychomycoses and nail infections approximately 6 months are required. Griseofulvin is also used in veterinary medicine against ringworm (*Trichophyton*) infections.

Patent application WO 97/05870 discloses the use of griseofulvin for inhibiting the growth of cancers, particularly in humans. The compound can be used to inhibit the growth of leukemia, tumors and cancer cells. The disclosure of this application is restricted to griseofulvin alone.

Oda discloses in J. Antibiot. 59(2), pages 114-116 (2006) that an analogue of griseofulvin in which the methoxy group in 2' position has been replaced by a n-propoxy group exhibits a stronger inhibiting effect on cancer cells than griseofulvin itself L. Mir et al. report an enhanced effect on cancer cells for 2'-(2-iodoethoxy)griseofulvin (FEBS Letters 88 (1978) pages 259-263).

The inhibiting effect of griseofulvin and these derivatives, is, however, not regarded as being sufficient to allow their use in the treatment of cancer. In addition, none of the documents mentions an inhibition of centrosomal clustering by these compounds.

It is therefore an object of the present invention to provide compounds which may be active in the treatment of cancer and which should not be based on the cytotoxic traditional chemotherapy principles. A further object of the present invention is the provision of methods for treating cancer wherein, the anti-tumoral mode of action should not be based on the cytotoxic principles of traditional chemotherapy. Furthermore cancer cells should be effected more selectively compared to "normal" non-transformed cells of the body. In particular cases, the compounds should have improved properties for the treatment of cancer compared to the known griseofulvin or its anti-cancer activity tested analogues, with respect to their anti-tumor activity as well as with respect to the spectrum of cancers which can be treated.

It has been found that certain derivatives of griseofulvin that have aromatic or heterocyclic substituents in the 2'-position (which are preferably further substituted) and/or certain substituents in the 3'-position show an enhanced anti-tumor activity that is characterized by an inhibition of centrosomal clustering.

Some of these compounds are known, in particular as having antifungal or dermatological activity (see e.g. U.S. Pat. No. 3,102,123; JP-A 03-255081; I. E. Page and S. E. Staniforth, The Chemical Society, Chemical Society, Letchworth, Hert. (1962) 1292-1303; I. Dhanshri C. et al., Indian Journal of Chemistry Sect. A., 45 A (2006) 194-201), however, no anti-tumor activity is disclosed in these documents.

Accordingly, the object is attained by a compound according to the general formula (I)

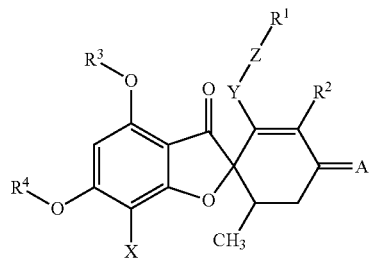

In the most general meaning classified below under I, the symbols have the following meanings.

I:
A is selected from: =O, =NOR$^5$, =N—NR$^6$R$^7$ or =NR$^8$,
X is halogen, hydrogen or pseudohalogen,
Y is —O—, —S—, a single bond, —NH—, —NR$^{11}$—, —N$^+$R$^{12}$R$^{13}$— or —C(O)—,
Z is —(CH$_2$)$_n$—,
n is an integer from 0 to 10,
R$^2$ is hydrogen, halogen, pseudohalogen, nitro, cyano, linear or branched (C$_1$-C$_5$)-alkyl, linear or branched (C$_2$-C$_5$)-alkenyl, linear or branched (C$_2$-C$_5$)-alkynyl, (C$_3$-C$_6$)-cycloalkyl, (C$_1$-C$_4$)-alkyloxy-(C$_1$-C$_4$)-alkyl, hydroxyl-(C$_1$-C$_4$)-alkyl, halogen-(C$_1$-C$_4$)-alkyl, amino, (C$_1$-C$_4$)-alkylamino, di(C$_1$-C$_4$)-alkylamino, (C$_1$-C$_4$)-alkylcarbonyl amino, (C$_1$-C$_4$)-alkyl sulfonyl amino, (C$_1$-C$_4$)-alkyl carbonyl, hydroxyl carbonyl, (C$_1$-C$_4$)-alkyloxy carbonyl, (C$_5$-C$_{10}$)-aryloxy carbonyl, amino carbonyl, (C$_1$-C$_4$)-alkylamino carbonyl, di-(C$_1$-C$_4$)-alkylamino carbonyl, hydroxy sulfonyl, amino sulfonyl, $(C_1-C_4)$-alkylamino sulfonyl and di-$(C_1-C_4)$-alkylamino sulfonyl, $R^1$ is, in case $R^2$ is hydrogen and n is other than 0: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and aromatic or non-aromatic heterocyclyl group are substituted on one or more ring carbon atoms by identical or different substituents $R^{10}$, $R^1$ is, in case $R^2$ is hydrogen and n is 0: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are unsubstituted or substituted on one or more ring carbon atoms by identical or different substituents $R^{10}$, $R^1$ is, in case $R^2$ is other than hydrogen: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are unsubstituted or substituted on one or more ring carbon atoms by identical or different substituents $R^{10}$, hydrogen, linear or branched $(C_1-C_{10})$-alkyl, linear or branched $(C_2-C_{10})$-alkenyl, linear or branched $(C_2-C_{10})$-alkynyl, $(C_3-C_7)$-cycloalkyl, wherein the named groups are unsubstituted or carry one or more substituent(s) from the group halogen, pseudohalogen, hydroxycarbonyl, nitro, amino, hydroxyl and hydroxyl-$(C_1-C_4)$-alkyl, $R^9$ is methyl, ethyl, propyl, iso-propyl, butyl, sec-butyl or tert-butyl, $R^{10}$ is halogen, pseudo halogen, nitro, cyano, linear or branched $(C_1-C_{10})$-alkyl, linear or branched $(C_2-C_{10})$-alkenyl, linear or branched $(C_2-C_{10})$-alkynyl, $(C_3-C_7)$-cycloalkyl, phenyl or naphthyl unsubstituted or substituted on one or more ring carbon atoms by identical or different substituents $R^{14}$, hydroxyl, $(C_1-C_4)$-alkyloxy, $(C_1-C_4)$-alkyloxy-$(C_1-C_4)$-alkyl, hydroxyl-$(C_1-C_4)$-alkyl, halogen-$(C_1-C_4)$-alkyl, amino, $(C_1-C_4)$-alkylamino, di$(C_1-C_4)$-alkylamino, $(C_1-C_4)$-alkylcarbonyl amino, $(C_1-C_4)$-alkyl sulfonyl amino, $(C_1-C_4)$-alkyl carbonyl, hydroxyl carbonyl, $(C_1-C_4)$-alkyloxycarbonyl, $(C_5-C_{10})$-aryloxycarbonyl, amino carbonyl, $(C_1-C_4)$-alkylamino carbonyl, di-$(C_1-C_4)$-alkylamino carbonyl, hydroxy sulfonyl, amino sulfonyl, $(C_1-C_4)$-alkylamino sulfonyl and di-$(C_1-C_4)$-alkylamino sulfonyl, $R^3$ is hydrogen, methyl or ethyl, or halogen substituted methyl or ethyl carrying from 1 to 5 halogen substituents, $R^4$ is hydrogen, linear or branched $(C_1-C_{10})$-alkyl, linear or branched $(C_2-C_{10})$-alkenyl, linear or branched $(C_2-C_{10})$-alkynyl, $(C_3-C_7)$-cycloalkyl, $(C_5-C_{10})$-aryl or aralkyl comprising linear or branched $(C_1-C_{10})$-alkyl and $(C_5-C_{10})$-aryl wherein the named groups are unsubstituted or carry one or more halogen substituent(s), $R^5$, $R^6$, $R^7$, $R^8$, $R^{11}$, $R^{12}$ and $R^{13}$ are independently of each other hydrogen, linear or branched $(C_1-C_4)$-alkyl or $(C_1-C_4)$-alkylcarbonyl and $R^{14}$ independently has the same meaning as $R^{10}$.

Accordingly, in one aspect of the invention there is provided a compound of the formula (I) as described above, a pharmaceutically acceptable salt thereof, or a preferred embodiment thereof for use in a method for treating cancer in a patient, preferably by administering to a patient suffering from said disease in a therapeutically effective amount a compound of formula (I) and/or a pharmaceutically acceptable salt thereof.

Alkyl, alkenyl and alkynyl groups can be linear, i.e. straight-chain, or branched. This also applies when they are part of other groups, for example alkyloxy groups (=alkoxy groups, i.e. alkyl-O— groups), alkyloxycarbonyl groups or alkyl-substituted amino groups, or when they are substituted. Examples of alkyl groups are methyl, ethyl, propyl, butyl, pentyl, hexyl, the n-isomers of these groups, isopropyl, isobutyl, isopentyl, sec-butyl, tert-butyl, neopentyl or 3,3-dimethylbutyl. Alkenyl groups and alkynyl groups preferably contain one double bond or triple bond, respectively, which can be present in any desired position of the group. Examples of alkenyl and alkynyl are prop-1-enyl, prop-2-enyl (=allyl), but-2-enyl, 2-methylprop-2-enyl, 3-methylbut-2-enyl, hex-3-enyl, hex-4-enyl, prop-2-ynyl (=propargyl), but-2-ynyl, but-3-ynyl, hex-4-ynyl or hex-5-ynyl.

As far as applicable, the preceding explanations regarding alkyl groups apply correspondingly to divalent alkyl, i.e. alkanediyl (alkylene) groups, such as the methylene group —$CH_2$— and the groups —$CH_2$—$CH_2$— and —$CH_2$—$CH_2$—$CH_2$—. As far as applicable, these groups can also be linear or branched. Examples of the group $C_nH_{2n}$, in which the number n is 1, 2, or 3, are —$CH_2$—, —$CH_2$—$CH_2$—, —$CH_2$—$CH_2$—$CH_2$—, —$CH(CH_3)$—, —$C(CH_3)_2$—, —$CH(CH_3)$—$CH_2$—, —$CH_2$—$CH(CH_3)$—. If the number n in the group $C_nH_{2n}$ is 0 (=zero), the groups which are attached to the group $C_nH_{2n}$ are directly connected to one another via a single bond.

Examples of cycloalkyl groups are cyclopropyl, cyclobutyl, cyclopentyl, cyclohexyl and cycloheptyl. In general, all cycloalkyl groups can also carry one or two identical or different $(C_1-C_4)$-alkyl substituents, for example methyl substituents, which can be located in any desired positions. Examples of alkyl-substituted cycloalkyl groups are 4-methylcyclohexyl, 4-tert-butylcyclohexyl or 2,3-dimethylcyclopentyl.

Groups like phenyl, naphthalenyl (=naphthyl) and heterocyclyl can be unsubstituted or substituted. If such a group is substituted by one or more substituents, it can carry for example one, two, three, four or five identical or different substituents. The substituents can be located in any desired position. Substituted heterocyclyl groups can be substituted on ring carbon atoms and/or on suitable ring nitrogen atoms, i.e. ring nitrogen atoms which in the parent ring system carry a hydrogen atom. Preferred substituents on such substituted ring nitrogen atoms are alkyl groups, for example $(C_1-C_4)$-alkyl groups, unless stated otherwise. Suitable ring nitrogen atoms, such as the ring nitrogen atoms in a pyridine ring or a quinoline ring, can also be present as N-oxides or as quaternary salts, the latter preferably having a counter-anion which is derived from a physiologically acceptable acid.

In monosubstituted phenyl groups, the substituent can be located in the 2-position, the 3-position or the 4-position. In a disubstituted phenyl group, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. Naphthalenyl can be naphthalen-1-yl or naphthalen-2- yl. In monosubstituted naphthalen-1-yl groups, the substituent can be located in the 2-, 3-, 4-, 5-, 6-, 7-, or 8-position, in monosubstituted naphthalen-2-yl groups, the substituent can be located in the 1-, 3-, 4-, 5-, 6-, 7-, or 8-position. In disubstituted naphthalenyl groups, the substituents can likewise occur in any desired positions in the ring via which the naphthalenyl group is bonded, and/or in the other ring.

Heteroaryl groups (i.e. aromatic heterocyclyl groups) are preferably 5-membered or 6-membered monocyclic aromatic heterocyclic groups or 9-membered or 10-membered bicyclic aromatic heterocyclic groups, where the bicyclic groups contain a 6-membered ring fused to a 5-membered or two fused 6-membered rings. In bicyclic heteroaryl groups, one or both rings can be aromatic and one or both rings can contain hetero ring members. Preferably heteroaryl groups and other heterocyclic groups contain one, two, three or four, preferably one, two or three, in particular one or two, identical or different ring hetero ring members. The ring heteroatoms in heteroaryl groups and other heterocyclic groups are chosen from N, O and S, wherein N includes ring nitrogen atoms which carry a hydrogen atom or any substituent as is the case in 5-membered aromatic heterocycles such as pyrrole, pyrazole or imidazole, for example. The heteroatoms in heteroaryl groups and other heterocyclic groups can be located in any desired positions provided that the resulting heterocyclic system is known in the art and is stable and suitable as a subgroup in a drug substance. For example, in general two atoms from the series O and S cannot be present in adjacent ring positions. Examples of parent heterocycles of heteroaryl groups and other heterocyclic groups are pyrrole, furan, thiophene, imidazole, pyrazole, 1,2,3-triazole, 1,2,4-triazole, oxazole (=1,3-oxazole), isoxazole (=1,2-oxazole), thiazole (=1,3-thiazole), isothiazole (=1,2-thiazole), tetrazole, pyridine, pyridazine, pyrimidine, pyrazine, 1,2,3-triazine, 1,2,4-triazine, 1,3,5-triazine, 1,2,4,5-tetrazine, indole, benzothiophene, benzofuran, 1,3-benzodioxole (=1,2-methylenedioxybenzene), 1,3-benzoxazole, 1,3-benzothiazole, benzoimidazole, chroman, isochroman, 1,4-benzodioxane (=1,2-ethylenedioxybenzene), quinoline, isoquinoline, cinnoline, quinazoline, quinoxaline, phthalazine, thienothiophenes, 1,8-naphthyridine and other naphthyridines, or pteridine. Heteroaryl and other heterocyclic groups can be bonded via any desired suitable ring carbon atom and, in the case of nitrogen heterocycles, ring nitrogen atom. Preferably they are bonded via a ring carbon atom. For example, thiophenyl (=thienyl) can be thiophen-2-yl or thiophen-3-yl, pyridinyl (=pyridyl) can be pyridin-2-yl, pyridin-3-yl or pyridin-4-yl, imidazolyl can be, for example, 1H-imidazol-1-yl, 1H-imidazol-2-yl, 1H-imidazol-4-yl or 1H-imidazol-5-yl, quinolinyl (=quinolyl) can be quinolin-2-yl, quinolin-3-yl, quinolin-4-yl, quinolin-5-yl, quinolin-6-yl, quinolin-7-yl or quinolin-8-yl. In monosubstituted pyridin-2-yl the substituent can be located in the 3-position, 4-position, 5-position or 6-position, in monosubstituted pyridin-3-yl the substituent can be located in the 2-position, 4-position, 5-position or 6-position, in monosubstituted pyridin-4-yl the substituent can be located in the 2-position or 3-position.

With regard to bicyclic systems that contain an aromatic ring and a non-aromatic ring, such systems are regarded as aromatic if they are bonded through the aromatic ring and as non-aromatic if they are bonded through the non-aromatic ring.

Preferred heteroaryl groups are pyrrole, furan, thiophene, imidazole, pyrazole, 1,2,3-triazole, 1,2,4-triazole, oxazole (=1,3-oxazole), isoxazole (=1,2-oxazole), thiazole (=1,3-thiazole), isothiazole (=1,2-thiazole), tetrazole, pyridine, pyridazine, pyrimidine, pyrazine, indole, benzothiophene, benzofuran, 1,3-benzodioxole (=1,2-methylenedioxybenzene), 1,3-benzoxazole, benzoimidazole, quinoline, isoquinoline.

Non-aromatic heterocyclic rings can be 4-membered, 5-membered, 6-membered, 7-membered, 8-membered, 9-membered or 10-membered, and can be saturated, i.e. contain no double bond within the ring, or unsaturated, including partially unsaturated and partially aromatic (i.e. in a bicyclic ring system one ring is aromatic), in particular partially unsaturated, and contain, for example, one, two, three or four double bonds within the ring, provided the respective ring system is known in the art to be stable and suitable as a subgroup in a drug substance. Examples are azetidinyl, pyrrolidinyl, 2,5-dihydro-1H-pyrrolyl, piperidinyl, 1,2,3,4-tetrahydropyridinyl, 1,2,5,6-tetrahydropyridinyl, 1,2-dihydropyridinyl, azepanyl, azocanyl, azecanyl, octahydrocyclopenta[b]pyrrolyl, 2,3-dihydro-1H-indolyl, octahydro-1H-indolyl, 2,3-dihydro-1H-isoindolyl, octahydro-1H-isoindolyl, 1,2-dihydroquinolinyl, 1,2,3,4-tetrahydroquinolinyl, decahydroquinolinyl, 1,2-dihydroisoquinolinyl, 1,2,3,4-tetrahydro isoquinolinyl, 1,2,3,4-tetrahydroisoquinolinyl, decahydroisoquinolinyl, decahydroisoquinolinyl, 4,5,6,7-tetrahydrothieno[3,2-c]pyridinyl, pyrazolidinyl, imidazolidinyl, hexahydropyrimidinyl, 1,2-dihydropyrimidinyl, piperazinyl, [1,3]diazepanyl, [1,4]diazepanyl, oxazolidinyl, [1,3]oxazinanyl, [1,3]oxazepanyl, morpholinyl, [1,4]oxazepanyl, thiazolidinyl, [1,3]thiazinanyl, thiomorpholinyl, 3,4-dihydro-2H-[1,4]thiazinyl, [1,3]thiazepanyl, [1,4]thiazepanyl, [1,4]thiazepanyl, oxiranyl, tetrahydrofuranyl, tetrahydrothienyl, isoxazolidinyl, isothiazolidinyl, oxazolidinyl, 1,2,4-oxadiazolidinyl, 1,2,4-thiadiazolidinyl, 1,2,4-triazolidinyl, 1,3,4-oxadiazolidinyl, 1,3,4-thiadiazolidinyl, 1,3,4-triazolidinyl, 2,3-dihydrofuranyl, 2,5-dihydrofuranyl, 2,3-dihydrothienyl, 2,5-dihydrothienyl, 2,3-dihydropyrrolyl, 2,3-dihydroisoxazolyl, 4,5-dihydroisoxazolyl, 2,5-dihydro isoxazolyl, 2,3-dihydroisothiazolyl, 4,5-dihydroisothiazolyl, 2,5-dihydroisothiazolyl, 2,3-dihydropyrazolyl, 4,5-dihydropyrazolyl, 2,5-dihydropyrazolyl, 2,3-dihydrooxazolyl, 4,5-dihydrooxazolyl, 2,5-dihydrooxazolyl, 2,3-dihydrothiazolyl, 4,5-dihydrothiazolyl, 2,5-dihydrothiazolyl, 2,3-dihydroimidazolyl, 4,5-dihydroimidazolyl, 2,5-dihydroimidazolyl, tetrahydropyridazinyl, tetrahydropyrimidinyl, tetrahydropyrazinyl, 1,3,5-tetrahydrotriazinyl, 1,3-dihydrooxazinyl, 1,3-dithianyl, tetrahydropyranyl, tetrahydrothiopyranyl, 1,3-dioxolanyl, 3,4,5,6-tetrahydropyridinyl, 4H-1,3-thiazinyl, 4H-3,1-benzothiazinyl, 1,1-dioxo-2,3,4,5-tetrahydrothienyl, 2H-1,4-benzothiazinyl, 2H-1,4-benzoxazinyl, 1,3-dihydrooxazinyl, and 2-oxy-5-azabicyclo[2.2.1]-heptan-5-yl.

Preferred non-aromatic heterocyclic rings are pyrrolidinyl, piperidinyl, 2,3-dihydro-1H-indolyl, pyrazolidinyl, imidazolidinyl, hexahydropyrimidinyl, piperazinyl, tetrahydropyridazinyl, tetrahydropyrimidinyl, tetrahydropyrazinyl.

In general, all listed examples of heterocyclic groups can be unsubstituted or substituted as indicated above, for example by $R^{10}$. For example, they can be substituted on one or more, for example one, two or three, preferably one or two, more preferably one, ring carbon atoms by oxo groups, and/or by one or more, for example one, two, three or four, preferably one or two, identical or different $(C_1-C_4)$-alkyl or $(C_1-C_7)$-cycloalkyl-$C_vH_{2v}$— (v=0, 1 or 2) groups, preferably $(C_1-C_4)$-alkyl groups, such as methyl groups, and/or on one or more ring nitrogen atom by a $(C_1-C_4)$-alkyl group or a $(C_1-C_4)$-alkyl-CO— group such as methyl or acetyl. Furthermore, ring sulfur atoms in the listed heterocyclic groups can carry one or two oxo groups, i.e. doubly bonded oxygen atoms, and thus become SO or $SO_2$ groups, i.e. sulfoxide or sulfone groups or S-oxides or S,S-dioxides.

Halogen is fluorine, chlorine, bromine or iodine, preferably fluorine, chlorine or bromine.

Pseudohalogen is —CN, —OCN, —NCO, —CNO, —SCN or —NSC.

An oxo group, when bonded to a carbon atom, replaces two hydrogen atoms on a carbon atom of the parent system. Thus, if a $CH_2$ group is substituted by oxo, i.e. by a doubly bonded oxygen atom, it becomes a CO group. Evidently, an oxo group cannot occur as a substituent on a carbon atom in an aromatic ring.

In a preferred embodiment of group I $R^2$ is hydrogen, n is other than 0 and $R^1$ is phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and aromatic or non-aromatic heterocyclyl group are substituted on one or more ring carbon atoms by identical or different substituents $R^{10}$.

In a further preferred embodiment of group I $R^2$ is hydrogen and n is 0 and $R^1$ is phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are unsubstituted or substituted on one or more ring carbon atoms by identical or different substituents $R^{10}$.

In a further preferred embodiment of group I $R^2$ is other than hydrogen and $R^1$ is phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are unsubstituted or substituted on one or more ring carbon atoms by identical or different substituents $R^{10}$, hydrogen, linear or branched ($C_1$-$C_{10}$)-alkyl, linear or branched ($C_2$-$C_{10}$)-alkenyl, linear or branched ($C_2$-$C_{10}$)-alkynyl, ($C_3$-$C_2$)-cycloalkyl, wherein the named groups are unsubstituted or carry one or more substituent(s) from the group halogen, pseudohalogen, hydroxycarbonyl, nitro, amino, hydroxyl and hydroxyl-($C_1$-$C_4$)-alkyl.

In a further preferred embodiment of group I $R^2$ is other than hydrogen and $R^1$ is phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are substituted on one or more ring carbon atoms by identical or different substituents $R^{10}$, linear or branched ($C_2$-$C_{10}$)-alkenyl, linear or branched ($C_2$-$C_{10}$)-alkynyl, ($C_3$-$C_7$)-cycloalkyl, wherein the named groups are unsubstituted or carry one or more substituent(s) from the group halogen, pseudohalogen, hydroxycarbonyl, nitro, amino, hydroxyl and hydroxyl-($C_1$-$C_4$)-alkyl.

Another preferred embodiment is classified below under II.

II:

A is selected from: =O, =$NOR^5$, =N—$NR^6R^7$ or —$NR^8$

X is Cl,

Y is —O—, —S—, a single bond, —NH—, —$NR^{11}$—, —$N^+R^{12}R^{13}$—, —C(O)—,

Z is —$(CH_2)_n$—, n is an integer from 0 to 10, $R^2$ is hydrogen, halogen, pseudohalogen, nitro, cyano, linear or branched ($C_1$-$C_5$)-alkyl, linear or branched ($C_2$-$C_5$)-alkenyl, linear or branched ($C_2$-$C_5$)-alkynyl, ($C_3$-$C_6$)-cycloalkyl, ($C_1$-$C_4$)-alkyloxy-($C_1$-$C_4$)-alkyl, hydroxyl-($C_1$-$C_4$)-alkyl, halogen-($C_1$-$C_4$)-alkyl, amino, ($C_1$-$C_4$)-alkylamino, di($C_1$-$C_4$)-alkylamino, ($C_1$-$C_4$)-alkylcarbonyl amino, ($C_1$-$C_4$)-alkyl sulfonyl amino, ($C_1$-$C_4$)-alkyl carbonyl, hydroxyl carbonyl, ($C_1$-$C_4$)-alkyloxy carbonyl, ($C_3$-$C_{10}$)-aryloxy carbonyl, amino carbonyl, ($C_1$-$C_4$)-alkylamino carbonyl, di-($C_1$-$C_4$)-alkylamino carbonyl, hydroxy sulfonyl, amino sulfonyl, ($C_1$-$C_4$)-alkylamino sulfonyl, and di-($C_1$-$C_4$)-alkylamino sulfonyl, $R^1$ is, in case $R^2$ is hydrogen and n is other than 0: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and aromatic or non-aromatic heterocyclyl group are substituted on one or more ring carbon atoms by identical or different substituents $R^{10}$, $R^1$ is, in case $R^2$ is hydrogen and n is 0: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are unsubstituted or substituted on one or more ring carbon atoms by identical or different substituents $R^{10}$, $R^1$ is, in case $R^2$ is halogen: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are unsubstituted or substituted on one or more ring carbon atoms by identical or different substituents $R^{10}$, hydrogen, linear or branched ($C_1$-$C_{10}$)-alkyl, linear or branched ($C_2$-$C_{10}$)-alkenyl, linear or branched ($C_2$-$C_{10}$)-alkynyl, ($C_3$-$C_7$)-cycloalkyl, wherein the named groups are unsubstituted or carry one or more substituent(s) from the group halogen, pseudohalogen, hydroxycarbonyl, nitro, amino, hydroxyl and hydroxyl-($C_1$-$C_4$)-alkyl, $R^9$ is methyl, ethyl, propyl, iso-propyl, butyl, sec-butyl or tert-butyl, $R^{10}$ is halogen, pseudo halogen, nitro, cyano, linear or branched ($C_1$-$C_{10}$)-alkyl, linear or branched ($C_2$-$C_{10}$)-alkenyl, linear or branched ($C_2$-$C_{10}$)-alkynyl, ($C_3$-$C_7$)-cycloalkyl, phenyl or naphthyl unsubstituted or substituted on one or more ring carbon atoms by identical or different substituents $R^{14}$, hydroxyl, ($C_1$-$C_4$)-alkyloxy, ($C_1$-$C_4$)-alkyloxy-($C_1$-$C_4$)-alkyl, hydroxyl-($C_1$-$C_4$)-alkyl, halogen-($C_1$-$C_4$)-alkyl, amino, ($C_1$-$C_4$)-alkylamino, di($C_1$-$C_4$)- alkylamino, $(C_1-C_4)$-alkylcarbonylamino, $(C_1-C_4)$-alkyl sulfonyl amino, $(C_1-C_4)$-alkyl carbonyl, hydroxyl carbonyl, $(C_1-C_4)$-alkyloxycarbonyl, $(C_5-C_{10})$-aryloxycarbonyl, amino carbonyl, $(C_1-C_4)$-alkylamino carbonyl, di-$(C_1-C_4)$-alkylamino carbonyl, hydroxy sulfonyl, amino sulfonyl, $(C_1-C_4)$-alkylamino sulfonyl and di-$(C_1-C_4)$-alkylamino sulfonyl, $R^3$ is hydrogen, methyl or ethyl, or halogen substituted methyl or ethyl carrying from 1 to 5 halogen substituents, $R^4$ independently has the same meaning as $R^3$, $R^5$, $R^6$, $R^7$, $R^8$, $R^{11}$, $R^{12}$ and $R^{13}$ are independently of each other H, linear or branched $(C_1-C_4)$-alkyl or $(C_1-C_4)$-alkylcarbonyl and $R^{14}$ independently has the same meaning as $R^{10}$.

Another preferred embodiment is classified below under III.

III:

A is =O,

X is Cl,

Y is —O—, —S— or a single bond,

Z is —$(CH_2)_n$—, n is an integer from 0 to 3, $R^2$ is hydrogen, halogen, pseudohalogen, nitro, cyano, linear or branched $(C_1-C_5)$-alkyl, linear or branched $(C_2-C_5)$-alkenyl, linear or branched $(C_2-C_5)$-alkynyl, $(C_3-C_6)$-cycloalkyl, $(C_1-C_4)$-alkyloxy-$(C_1-C_4)$-alkyl, hydroxyl-$(C_1-C_4)$-alkyl, halogen-$(C_1-C_4)$-alkyl, amino, $(C_1-C_4)$-alkylamino, di$(C_1-C_4)$-alkylamino, $(C_1-C_4)$-alkylcarbonyl amino, $(C_1-C_4)$-alkyl sulfonyl amino, $(C_1-C_4)$-alkyl carbonyl, hydroxyl carbonyl, $(C_1-C_4)$-alkyloxy carbonyl, $(C_3-C_{10})$-aryloxy carbonyl, amino carbonyl, $(C_1-C_4)$-alkylamino carbonyl, di-$(C_1-C_4)$-alkylamino carbonyl, hydroxy sulfonyl, amino sulfonyl, $(C_1-C_4)$-alkylamino sulfonyl and di-$(C_1-C_4)$-alkylamino sulfonyl, $R^1$ is, in case $R^2$ is hydrogen and n is other than 0: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and aromatic or non-aromatic heterocyclyl group are substituted on one or more ring carbon atoms by identical or different substituents $R^{10}$, $R^1$ is, in case $R^2$ is hydrogen and n is 0: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are unsubstituted or substituted on one or more ring carbon atoms by identical or different substituents $R^{10}$, $R^1$, is in case $R^2$ is iodine: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are unsubstituted or substituted on one or more ring carbon atoms by identical or different substituents $R^{10}$, hydrogen, linear or branched $(C_1-C_{10})$-alkyl, linear or branched $(C_2-C_{10})$-alkenyl, linear or branched $(C_2-C_{10})$-alkynyl, $(C_3-C_7)$-cycloalkyl, wherein the named groups are unsubstituted or carry one or more substituent(s) from the group halogen, pseudohalogen, hydroxycarbonyl, nitro, amino, hydroxyl and hydroxyl-$(C_1-C_4)$-alkyl, $R^9$ is methyl, ethyl, propyl, iso-propyl, butyl, sec-butyl or tert-butyl, $R^{10}$ is halogen, pseudo halogen, nitro, cyano, linear or branched $(C_1-C_{10})$-alkyl, linear or branched $(C_2-C_{10})$-alkenyl, linear or branched $(C_2-C_{10})$-alkynyl, $(C_3-C_7)$-cycloalkyl, phenyl or naphthyl unsubstituted or substituted on one or more ring carbon atoms by identical or different substituents $R^{14}$, hydroxyl, $(C_1-C_4)$-alkyloxy, $(C_1-C_4)$-alkyloxy-$(C_1-C_4)$-alkyl, hydroxyl-$(C_1-C_4)$-alkyl, halogen-$(C_1-C_4)$-alkyl, amino, $(C_1-C_4)$-alkylamino, di$(C_1-C_4)$-alkylamino, $(C_1-C_4)$-alkylcarbonyl amino, $(C_1-C_4)$-alkyl sulfonyl amino, $(C_1-C_4)$-alkyl carbonyl, hydroxyl carbonyl, $(C_1-C_4)$-alkyloxycarbonyl, $(C_5-C_{10})$-aryloxycarbonyl, amino carbonyl, $(C_1-C_4)$-alkylamino carbonyl, di-$(C_1-C_4)$-alkylamino carbonyl, hydroxy sulfonyl, amino sulfonyl, $(C_1-C_4)$-alkylamino sulfonyl and di-$(C_1-C_4)$-alkylamino sulfonyl, $R^3$ is hydrogen, methyl or ethyl, or halogen substituted methyl or ethyl carrying from 1 to 5 halogen substituents, $R^4$ independently has the same meaning as $R^3$, $R^{14}$ independently has the same meaning as $R^{10}$.

Another preferred embodiment is classified below under IV.

IV:

A is =O,

X is Cl,

Y is —O—, —S—,

Z is —$(CH_2)_n$—, n is an integer from 0 to 3, $R^2$ is hydrogen, halogen, pseudohalogen, nitro, cyano, linear or branched $(C_1-C_5)$-alkyl, linear or branched $(C_2-C_5)$-alkenyl, linear or branched $(C_2-C_5)$-alkynyl, $(C_3-C_6)$-cycloalkyl, $(C_1-C_4)$-alkyloxy-$(C_1-C_4)$-alkyl, hydroxyl-$(C_1-C_4)$-alkyl, halogen-$(C_1-C_4)$-alkyl, amino, $(C_1-C_4)$-alkylamino, di$(C_1-C_4)$-alkylamino, $(C_1-C_4)$-alkylcarbonyl amino, $(C_1-C_4)$-alkyl sulfonyl amino, $(C_1-C_4)$-alkyl carbonyl, hydroxyl carbonyl, $(C_1-C_4)$-alkyloxy carbonyl, $(C_5-C_{10})$-aryloxy carbonyl, amino carbonyl, $(C_1-C_4)$-alkylamino carbonyl, di-$(C_1-C_4)$-alkylamino carbonyl, hydroxy sulfonyl, amino sulfonyl, $(C_1-C_4)$-alkylamino sulfonyl and di-$(C_1-C_4)$-alkylamino sulfonyl, $R^1$ is, in case $R^2$ is hydrogen and n is other than 0: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and aromatic or non-aromatic heterocyclyl group are substituted on one or more ring carbon atoms by identical or different substituents $R^{10}$, $R^1$ is, in case $R^2$ is hydrogen and n=0: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are unsubstituted or substituted on one or more ring carbon atoms by identical or different substituents $R^{10}$, R$^1$ is, in case R$^2$ is iodine: phenyl, naphthyl or an aromatic or non-aromatic, 5- to 10-membered monocyclic or bicyclic heterocyclyl group which contains 1, 2 or 3 identical or different ring heteroatoms selected from N, O or S wherein in case of N-containing heterocycles one of the ring nitrogen atoms is unsubstituted or carries a hydrogen atom or a substituent R$^9$, and wherein the phenyl, naphthyl and the aromatic or non-aromatic heterocyclyl group are unsubstituted or substituted on one or more ring carbon atoms by identical or different substituents R$^{10}$, hydrogen, linear or branched (C$_1$-C$_{10}$)-alkyl, linear or branched (C$_2$-C$_{10}$)-alkenyl, linear or branched (C$_2$-C$_{10}$)-alkynyl, (C$_1$-C$_7$)-cycloalkyl, wherein the named groups are unsubstituted or carry one or more substituent(s) from the group halogen, pseudohalogen, hydroxycarbonyl, nitro, amino, hydroxyl and hydroxyl-(C$_1$-C$_4$)-alkyl, R$^9$ is methyl, ethyl, propyl, iso-propyl, butyl, sec-butyl or tert-butyl, R$^{10}$ is halogen, pseudo halogen, nitro, cyano, linear or branched (C$_1$-C$_{10}$)-alkyl, linear or branched (C$_2$-C$_{10}$)-alkenyl, linear or branched (C$_2$-C$_{10}$)-alkynyl, (C$_3$-C$_7$)-cycloalkyl, phenyl or naphthyl unsubstituted or substituted on one or more ring carbon atoms by identical or different substituents R$^{14}$, hydroxyl, (C$_1$-C$_4$)-alkyloxy, (C$_1$-C$_4$)-alkyloxy-(C$_1$-C$_4$)-alkyl, hydroxyl-(C$_1$-C$_4$)-alkyl, halogen-(C$_1$-C$_4$)-alkyl, amino, (C$_1$-C$_4$)-alkylamino, di(C$_1$-C$_4$)-alkylamino, (C$_1$-C$_4$)-alkyl carbonyl amino, (C$_1$-C$_4$)-alkyl sulfonyl amino, (C$_1$-C$_4$)-alkyl carbonyl, hydroxyl carbonyl, (C$_1$-C$_4$)-alkyloxycarbonyl, (C$_5$-C$_{10}$)-aryloxycarbonyl, amino carbonyl, (C$_1$-C$_4$)-alkylamino carbonyl, di-(C$_1$-C$_4$)-alkylamino carbonyl, hydroxy sulfonyl, amino sulfonyl, (C$_1$-C$_4$)-alkylamino sulfonyl and di-(C$_1$-C$_4$)-alkylamino sulfonyl, R$^3$ is hydrogen, methyl or ethyl, or halogen substituted methyl or ethyl carrying from 1 to 5 halogen substituents, R$^4$ independently has the same meaning as R$^3$ and R$^{14}$ independently has the same meaning as R$^{10}$.

Another preferred embodiment is classified below under V.

V:

A is =O,

X is Cl,

Y is —O—, —S—,

Z is —(CH$_2$)$_n$—, n is an integer from 0 to 3,

R$^2$ is hydrogen

R$^1$ is, in case n is other than 0: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent R$^9$, and wherein the phenyl, naphthyl and aromatic or non-aromatic heterocyclyl group are substituted on one or more ring carbon atoms by identical or different substituents R$^{10}$, R$^1$ is, in case n is 0: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent R$^9$, and wherein the phenyl, naphthyl and the aromatic or non-aromatic heterocyclyl group are unsubstituted or substituted on one or more ring carbon atoms by identical or different substituents R$^{10}$, R$^9$ is methyl, ethyl, propyl, iso-propyl, butyl, sec-butyl or tert-butyl, R$^{10}$ is halogen, pseudo halogen, nitro, cyano, linear or branched (C$_1$-C$_{10}$)-alkyl, linear or branched (C$_2$-C$_{10}$)-alkenyl, linear or branched (C$_2$-C$_{10}$)-alkynyl, (C$_3$-C$_7$)-cycloalkyl, phenyl or naphthyl unsubstituted or substituted on one or more ring carbon atoms by identical or different substituents R$^{14}$, hydroxyl, (C$_1$-C$_4$)-alkyloxy, (C$_1$-C$_4$)-alkyloxy-(C$_1$-C$_4$)-alkyl, hydroxyl-(C$_1$-C$_4$)-alkyl, halogen-(C$_1$-C$_4$)-alkyl, amino, (C$_1$-C$_4$)-alkylamino, di(C$_1$-C$_4$)-alkylamino, (C$_1$-C$_4$)-alkylcarbonyl amino, (C$_1$-C$_4$)-alkyl sulfonyl amino, (C$_1$-C$_4$)-alkyl carbonyl, hydroxyl carbonyl, (C$_1$-C$_4$)-alkyloxycarbonyl, (C$_5$-C$_{10}$)-aryloxycarbonyl, amino carbonyl, (C$_1$-C$_4$)-alkylamino carbonyl, di-(C$_1$-C$_4$)-alkylamino carbonyl, hydroxy sulfonyl, amino sulfonyl, (C$_1$-C$_4$)-alkylamino sulfonyl and di-(C$_1$-C$_4$)-alkylamino sulfonyl, R$^3$ is hydrogen, methyl or ethyl, or halogen substituted methyl or ethyl carrying from 1 to 5 halogen substituents, R$^4$ independently has the same meaning as R$^3$, R$^{14}$ independently has the same meaning as R$^{10}$.

Another preferred embodiment is classified below under VI.

VI:

A is selected from: =O, =NOR$^5$, =N—NR$^6$R$^7$ or =NR$^8$,

X is Cl,

Y is —O—, —S—,

Z is —(CH$_2$)$_n$—, n is an integer from 0 to 2,

R$^2$ is hydrogen,

R$^1$ is phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent R$^9$, and wherein the phenyl, naphthyl and aromatic or non-aromatic heterocyclyl group are substituted on one or more ring carbon atoms by identical or different substituents R$^{10}$, R$^9$ is methyl, ethyl, propyl, iso-propyl, butyl, sec-butyl or tert-butyl, R$^{10}$ is halogen, pseudo halogen, nitro, cyano, linear or branched (C$_1$-C$_5$)-alkyl, linear or branched (C$_2$-C$_5$)-alkenyl, linear or branched (C$_2$-C$_5$)-alkynyl, (C$_3$-C$_7$)-cycloalkyl, phenyl or naphthyl, hydroxyl, (C$_1$-C$_4$)-alkyloxy, (C$_1$-C$_4$)-alkyloxy-(C$_1$-C$_4$)-alkyl, hydroxyl-(C$_1$-C$_4$)-alkyl, halogen-(C$_1$-C$_4$)-alkyl, amino, (C$_1$-C$_4$)-alkylamino, di(C$_1$-C$_4$)-alkylamino, (C$_1$-C$_4$)-alkylcarbonyl amino, (C$_1$-C$_4$)-alkyl sulfonyl amino, (C$_1$-C$_4$)-alkyl carbonyl, hydroxyl carbonyl, (C$_1$-C$_4$)-alkyloxycarbonyl, (C$_5$-C$_{10}$)-aryloxycarbonyl, amino carbonyl, (C$_1$-C$_4$)-alkylamino carbonyl, di-(C$_1$-C$_4$)-alkylamino carbonyl, hydroxy sulfonyl, amino sulfonyl, (C$_1$-C$_4$)-alkylamino sulfonyl and di-(C$_1$-C$_4$)-alkylamino sulfonyl, R$^3$ is hydrogen, methyl or ethyl, or halogen substituted methyl or ethyl carrying from 1 to 5 halogen substituents, R$^4$ independently has the same meaning as R$^3$ and R$^5$, R$^6$, R$^7$ and R$^8$ are independently of each other H, linear or branched (C$_1$-C$_4$)-alkyl or (C$_1$-C$_4$)-alkylcarbonyl.

Another preferred embodiment is classified below under VII.

VII:

A is selected from: =O, =NOR$^5$, =N—NR$^6$R$^7$ or =NR$^8$,

X is Cl,

Y is —O—, —S—,

Z is —(CH$_2$)$_n$—, n is an integer from 1 to 2,

R$^2$ is hydrogen,

R¹ is phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and aromatic or non-aromatic heterocyclyl group are substituted on one or more ring carbon atoms by identical or different substituents $R^{10}$, $R^9$ is methyl, ethyl, propyl, iso-propyl, butyl, sec-butyl or tert-butyl, $R^{10}$ is halogen, pseudo halogen, nitro, cyano, linear or branched $(C_1$-$C_{10})$-alkyl, linear or branched $(C_2$-$C_{10})$-alkenyl, linear or branched $(C_2$-$C_{10})$-alkynyl, $(C_3$-$C_7)$-cycloalkyl, phenyl or naphthyl unsubstituted or substituted on one or more ring carbon atoms by identical or different substituents $R^{14}$, hydroxyl, $(C_1$-$C_4)$-alkyloxy, $(C_1$-$C_4)$-alkyloxy-$(C_1$-$C_4)$-alkyl, hydroxyl-$(C_1$-$C_4)$-alkyl, halogen-$(C_1$-$C_4)$-alkyl, amino, $(C_1$-$C_4)$-alkylamino, di$(C_1$-$C_4)$-alkylamino, $(C_1$-$C_4)$-alkylcarbonyl amino, $(C_1$-$C_4)$-alkyl sulfonyl amino, $(C_1$-$C_4)$-alkyl carbonyl, hydroxyl carbonyl, $(C_1$-$C_4)$-alkyloxycarbonyl, $(C_5$-$C_{10})$-aryloxycarbonyl, amino carbonyl, $(C_1$-$C_4)$-alkylamino carbonyl, di-$(C_1$-$C_4)$-alkylamino carbonyl, hydroxy sulfonyl, amino sulfonyl, $(C_1$-$C_4)$-alkylamino sulfonyl and di-$(C_1$-$C_4)$-alkylamino sulfonyl, $R^3$ is hydrogen, methyl or ethyl, or halogen substituted methyl or ethyl carrying from 1 to 5 halogen substituents, $R^4$ independently has the same meaning as $R^3$, $R^5$, $R^6$, $R^7$ and $R^8$ are independently of each other H, linear or branched $(C_1$-$C_4)$-alkyl or $(C_1$-$C_4)$-alkylcarbonyl, $R^{14}$ independently has the same meaning as $R^{10}$.

Another preferred embodiment is classified below under VIII.

VIII:

A is selected from: =O, =NOR⁵, =N—NR⁶R⁷ or =NR⁸,

X is Cl,

Y is —O—, —S—,

Z is —$(CH_2)_n$—, n is an integer from 1 to 2,

R² is hydrogen,

R¹ is phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and aromatic or non-aromatic heterocyclyl group are substituted on one or more ring carbon atoms by identical or different substituents $R^{10}$, $R^9$ is methyl, ethyl, propyl, iso-propyl, butyl, sec-butyl or tert-butyl, $R^{10}$ is halogen, pseudo halogen, nitro, cyano, linear or branched $(C_1$-$C_{10})$-alkyl, linear or branched $(C_2$-$C_5)$-alkenyl, linear or branched $(C_2$-$C_5)$-alkynyl, $(C_1$-$C_7)$-cycloalkyl, phenyl or naphthyl, hydroxyl, $(C_1$-$C_4)$-alkyloxy, $(C_1$-$C_4)$-alkyloxy-$(C_1$-$C_4)$-alkyl, hydroxyl-$(C_1$-$C_4)$-alkyl, halogen-$(C_1$-$C_4)$-alkyl, amino, $(C_1$-$C_4)$-alkylamino, di$(C_1$-$C_4)$-alkylamino, $(C_1$-$C_4)$-alkylcarbonyl amino, $(C_1$-$C_4)$-alkyl sulfonyl amino, $(C_1$-$C_4)$-alkyl carbonyl, hydroxyl carbonyl, $(C_1$-$C_4)$-alkyloxycarbonyl, $(C_5$-$C_{10})$-aryloxycarbonyl, amino carbonyl, $(C_1$-$C_4)$-alkylamino carbonyl, di-$(C_1$-$C_4)$-alkylamino carbonyl, hydroxy sulfonyl, amino sulfonyl, $(C_1$-$C_4)$-alkylamino sulfonyl and di-$(C_1$-$C_4)$-alkylamino sulfonyl, $R^3$ is hydrogen, methyl or ethyl, or halogen substituted methyl or ethyl carrying from 1 to 5 halogen substituents, $R^4$ independently has the same meaning as $R^3$ and $R^5$, $R^6$, $R^7$ and $R^8$ are independently of each other H, linear or branched $(C_1$-$C_4)$-alkyl or $(C_1$-$C_4)$-alkylcarbonyl.

In a further aspect of the invention there is provided a compound of formula (I), where the symbols have the following meanings:

A is selected from: =O, =NOR⁵, =N—NR⁶R⁷ or =NR⁸,

X is halogen, hydrogen or pseudohalogen,

Y is —O—, —S—, a single bond, —NH—, —NR¹¹—, —N⁺R¹²R¹³— or —C(O)—,

Z is —$(CH_2)_n$—, n is an integer from 0 to 10,

R² is hydrogen, halogen, pseudohalogen, nitro, cyano, linear or branched $(C_1$-$C_4)$-alkyl, linear or branched $(C_2$-$C_5)$-alkenyl, linear or branched $(C_2$-$C_5)$-alkynyl, $(C_3$-$C_6)$-cycloalkyl, $(C_1$-$C_4)$-alkyloxy-$(C_1$-$C_4)$-alkyl, hydroxyl-$(C_1$-$C_4)$-alkyl, halogen-$(C_1$-$C_4)$-alkyl, amino, $(C_1$-$C_4)$-alkylamino, di$(C_1$-$C_4)$-alkyl amino, $(C_1$-$C_4)$-alkyl carbonyl amino, $(C_1$-$C_4)$-alkyl sulfonyl amino, $(C_1$-$C_4)$-alkyl carbonyl, hydroxyl carbonyl, $(C_1$-$C_4)$-alkyloxy carbonyl, $(C_5$-$C_{10})$-aryloxy carbonyl, amino carbonyl, $(C_1$-$C_4)$-alkylamino carbonyl, di-$(C_1$-$C_4)$-alkylamino carbonyl, hydroxy sulfonyl, amino sulfonyl, $(C_1$-$C_4)$-alkylamino sulfonyl and di-$(C_1$-$C_4)$-alkylamino sulfonyl, R¹ is, in case R² is hydrogen and n is other than 0: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and aromatic or non-aromatic heterocyclyl group are substituted on one or more ring carbon atoms by identical or different substituents $R^{10}$, R¹ is, in case R² is hydrogen and n is 0: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are substituted on one or more ring carbon atoms by identical or different substituents $R^{10}$, R¹ is, in case R² is other than hydrogen: phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are unsubstituted or substituted on one or more ring carbon atoms by identical or different substituents $R^{10}$, linear or branched $(C_2$-$C_{10})$-alkenyl, linear or branched $(C_2$-$C_{10})$-alkynyl, $(C_3$-$C_7)$-cycloalkyl, wherein the named groups are unsubstituted or carry one or more substituent(s) from the group halogen, pseudohalogen, hydroxycarbonyl, nitro, amino, hydroxyl and hydroxyl-$(C_1$-$C_4)$-alkyl, $R^9$ is methyl, ethyl, propyl, iso-propyl, butyl, sec-butyl or tert-butyl, $R^{10}$ is halogen, pseudo halogen, nitro, cyano, linear or branched $(C_1$-$C_{10})$-alkyl, linear or branched $(C_2$-$C_{10})$-alkenyl, linear or branched $(C_2$-$C_{10})$-alkynyl, $(C_1$-$C_7)$-cycloalkyl, phenyl or naphthyl unsubstituted or substituted on one or more ring carbon atoms by identical or different substituents $R^{14}$, hydroxyl, $(C_1-C_4)$-alkyloxy, $(C_1-C_4)$-alkyloxy-$(C_1-C_4)$-alkyl, hydroxyl-$(C_1-C_4)$-alkyl, halogen-$(C_1-C_4)$-alkyl, amino, $(C_1-C_4)$-alkylamino, di$(C_1-C_4)$-alkylamino, $(C_1-C_4)$-alkylcarbonyl amino, $(C_1-C_4)$-alkyl sulfonyl amino, $(C_1-C_4)$-alkyl carbonyl, hydroxyl carbonyl, $(C_1-C_4)$-alkyloxycarbonyl, $(C_5-C_{10})$-aryloxycarbonyl, amino carbonyl, $(C_1-C_4)$-alkylamino carbonyl, di-$(C_1-C_4)$-alkylamino carbonyl, hydroxy sulfonyl, amino sulfonyl, $(C_1-C_4)$-alkylamino sulfonyl and di-$(C_1-C_4)$-alkylamino sulfonyl, $R^3$ is hydrogen, methyl or ethyl, or halogen substituted methyl or ethyl carrying from 1 to 5 halogen substituents, $R^4$ is hydrogen, linear or branched $(C_1-C_{10})$-alkyl, linear or branched $(C_2-C_{10})$-alkenyl, linear or branched $(C_2-C_{10})$-alkynyl, $(C_3-C_7)$-cycloalkyl, $(C_5-C_{10})$-aryl or aralkyl comprising linear or branched $(C_1-C_{10})$-alkyl and $(C_5-C_{10})$-aryl wherein the named groups are unsubstituted or carry one or more halogen substituent(s), $R^5$, $R^6$, $R^7$, $R^8$, $R^{11}$, $R^{12}$ and $R^{13}$ are independently of each other hydrogen, linear or branched $(C_1-C_4)$-alkyl or $(C_1-C_4)$-alkylcarbonyl and $R^{14}$ independently has the same meaning as $R^{10}$.

In a preferred embodiment of the novel compounds of formula (I) $R^2$ is hydrogen, n is other than 0 and $R^1$ is phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and aromatic or non-aromatic heterocyclyl group are substituted on one or more ring carbon atoms by identical or different substituents $R^{10}$.

In a further preferred embodiment of the novel compounds of formula (I) $R^2$ is hydrogen, n is 0 and $R^1$ is phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are substituted on one or more ring carbon atoms by identical or different substituents $R^{10}$.

In a further preferred embodiment of the novel compounds of formula (I) $R^2$ is other than hydrogen and $R^1$ is phenyl, naphthyl or an aromatic or non-aromatic, 5- to 10-membered monocyclic or bicyclic heterocyclyl group which contains 1, 2 or 3 identical or different ring heteroatoms selected from N, O and S wherein in case of N-containing heterocycles one of the ring nitrogen atoms is unsubstituted or carries a hydrogen atom or a substituent $R^9$, and wherein the phenyl, naphthyl and the aromatic or non-aromatic heterocyclyl group are unsubstituted or substituted on one or more ring carbon atoms by identical or different substituents $R^{10}$, linear or branched $(C_2-C_{10})$-alkenyl, linear or branched $(C_2-C_{10})$-alkynyl, $(C_3-C_7)$-cycloalkyl, wherein the named groups are unsubstituted or carry one or more substituent(s) from the group halogen, pseudohalogen, hydroxycarbonyl, nitro, amino, hydroxyl and hydroxyl-$(C_1-C_4)$-alkyl.

Within the definitions made beforehand for embodiments I to VIII, the individual meanings for each substituent or each group are not construed to be restricted to the embodiment under which it is mentioned, i.e. a definition cited under III may be combined with the definitions made under e.g. I, II, or III. The entire combination of all the definitions for each substituent made under each of I to VIII is however preferred.

As an example, for the best known compound close to the formula (I) and which is not included in the present invention is griseofulvin according to the formula (II)

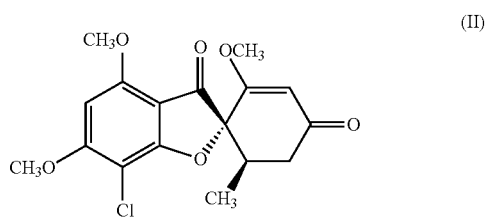

(II)

The cancer varieties which can be treated with the compounds as defined beforehand are human malignancies, preferably solid neoplasias or haematological malignancies. Examples for such malignancies comprise brain cancer, head- and neck cancer, renal cancer, breast cancer, esophageal cancer, gastric cancer, colon cancer, liver cancer, lung cancer, pancreas cancer, biliary tract cancer, prostate cancer, skin cancer, melanoma, ovarian cancer, cervical cancer, sarcoma, bone and soft tissue sarcomas, leukemia, multiple myeloma and lymphoma, including both Hodgkin and Non-Hodgkin lymphomas.

Basically, all human malignancies are potential targets for centrosomal cluster inhibitors/griseofulvin/griseofulvin analogues since almost all malignant neoplasias examined to date harbour centrosome aberrations. Specifically, centrosome aberrations have been reported in solid tumors of different origin including brain, breast, lung, cervical colon, pancreatic, biliary tract, prostate, and head and neck cancers. Also, sarcomas and hematological malignancies including Hodgkin and Non-Hodgkin lymphomas, acute and chronic myeloid leukemias, chronic lymphocytic leukemias and multiple myelomas have been described to harbour centrosomal abnormalities. Importantly, since several preneoplastic lesions like, cervical intraepithelial neoplasias, ductal carcinoma in situ of the mammary gland, colon and pancreatic adenomas, pre-invasive carcinomas in situ of the prostate, myelodysplastic syndromes, and monoclonal gammopathies of undetermined significance contain centrosome aberrations as well, the above therapy might also serve to prevent progression of these lesions into invasive carcinomas, leukaemia or multiple myeloma, respectively.

In a further embodiment, the present invention relates to a compound according to formula (I) as defined above in general form or in preferred embodiments, or a pharmaceutically acceptable salt thereof, for use as medicament.

The term "pharmaceutical composition" is sometimes referred to as "pharmaceutical" or "medicament" hereinafter or in the prior art. Said terms shall have the same meaning and may be used interchangeably.

The compounds according to the formula (I) act as an inhibitor of centrosome clustering. They force tumor cells with supernumerary centrosomes to undergo multipolar mitoses and, subsequently, apoptosis.

Moreover, the compounds are specific for the tumours because they elicit no or only minor specific side effects on healthy body cells with a normal centrosome content. Accordingly, there are no or only minor side effects to be expected.

Centrosomes are small cytoplasmic organelles which consist of a pair of centrioles embedded in pericentriolar material and act as microtubule organizing centers. During mitosis, centrosomes function as spindle poles, directing the formation of bipolar spindles, a process essential for accurate chromosome segregation. Since the centrosome duplicates precisely once per cell cycle, each daughter cell receives one centrosome upon cytokinesis and contains two centrosomes at the time of mitosis.

Centrosome amplification has been frequently observed in both solid tumors and hematological malignancies and is linked to tumorigenesis and aneuploidy. The extent of centrosomal aberrations is correlated with the degree of chromosomal instability and clinical aggressiveness of the malignant neoplasias. In mitosis, supernumerary centrosomes can lead to the formation of multipolar spindles which are responsible for chromosome malsegregation with subsequent aneuploidy and which can be found in many tumor types. Multipolar spindles, however, are antagonistic to cell viability. Most progeny derived from a defective mitosis will undergo apoptosis, but few daughter cells, receiving the appropriate chromosome complement and gene dosage, may survive and contribute, via clonal selection, to a population of aneuploid tumor cells. The survivors, however, must overcome the condition of supernumerary centrosomes in order to divide efficiently. To regain secondary karyotype stability, many tumor cells have developed a mechanism termed centrosomal clustering that prevents the formation of multipolar spindles by coalescence of multiple centrosomes into two functional spindle poles.

Centrosome positioning in the center of interphase cells is accomplished by pulling forces applied to microtubules by dynein, which serves to keep the centrosome away from the cell margin, and microtubule pushing by actomyosin-driven forces directed toward the cell center. Several pieces of evidence suggest that the minus-end-directed microtubule motor protein dynein is involved in microtubule minus end bundling for the establishment of bipolar spindles. A current model suggests that the function of dynein to tether spindle pole microtubules into bundles requires NuMA, which might use the motor activity of dynein to become localized to centrosomes. At the spindle poles, it forms a matrix to hold microtubule minus ends together. Analogous, in cells with multiple centrosomes, centrosomal clustering seems to be mediated by dynein. Recent data show that only cells with spindle-associated dynein localization were capable of coalescing multiple centrosomes into two spindle poles. Spindle multipolarity, on the other hand, was found to follow overexpression of NuMA which interferes with the spindle localization of dynein. With the exception of the involvement of dynein and NuMA, the molecular mechanisms responsible for clustering of multiple centrosomes into two spindle poles of tumor cells are unknown.

The only known small molecules that specifically affect the mitotic machinery target either tubulin or the plus-end-directed motor protein Eg5, a mitotic kinesin required for spindle bipolarity. Whereas vinca alkaloids and taxanes disrupt spindle function by inhibiting or increasing microtubule polymerization, inhibition of Eg5 activity by monastrol leads to impaired microtubule-dependent centrosome separation and formation of monopolar spindles. Both vinca alkaloids and taxanes are used as anticancer drugs and Eg5 is currently evaluated as a potential target for antineoplastic drug development. However, neither microtubule poisoning nor Eg5 inhibition selectively affects tumor cells, explaining side effects and dose limitations of antimitotic drugs in clinical use.

Supernumerary centrosomes do almost exclusively occur in a wide variety of neoplastic disorders but not in non-transformed cells. Therefore, inhibition of centrosomal clustering with consequential induction of multipolar spindles and subsequent cell death would specifically target tumor cells with no impact on normal cells with a regular centrosome content. To identify cell-permeable small molecules that inhibit centrosomal clustering in cells with supernumerary centrosomes, we developed a cell-based screening strategy founded on the visualization of microtubules and chromatin.

Natural products have proved to be rich sources of novel anti-cancer lead compounds during the past 20 years. Therefore, we decided to screen a fungal extract library for compounds inhibiting centrosomal clustering. The fungal extracts were selected based on a chemotaxonomic screening approach, in order to increase the chemodiversity to be tested. An initial screening effort using extracts from different *Penicillium* species led to the identification of griseofulvin as an inhibitor of centrosome coalescence in several different tumor cell lines.

The concentrations of the compounds used according to the present invention necessary for the induction of multipolar spindles are similar to those required for the inhibition of mitosis and cell proliferation, suggesting that multipolar spindles lead to aberrant cell divisions and subsequent cell death. The cytotoxicity induced by the compounds used according to the present invention is limited to cells with multipolar spindles. Unlike those, cells with bipolar spindles, despite experiencing a prolonged mitosis, eventually divide and survive in the presence of the compounds of the invention.

The compounds having a structure as shown in the general formula (I) are more potent than the known compound griseofulvin.

Specifically, growth, cell cycle and viability of "normal" non-transformed body cells is not affected by the compounds of the invention.

The present invention includes the use of all stereoisomeric forms of the compounds of the formula (I) for the purposes laid out herein, i.e. for the treatment of cancer, particular the cancer varieties which can be treated with a compound of the formula (I). The present invention also includes, for the compounds as defined beforehand which are not known, all stereoisomeric forms of these compounds. Centers of asymmetry that are present in the compounds of formula (I) all independently of one another have S configuration or R configuration. The invention includes all possible enantiomers and diastereomers and mixtures of two or more stereoisomers, for example mixtures of enantiomers and/or diastereomers, in all ratios. Thus, compounds according to the present invention which can exist as enantiomers can be present in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. All these forms are an object of the present invention. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the formula (I) or at the stage of an intermediate during the synthesis. The present invention also includes all tautomeric forms of the compounds of formula (I).

In case the compounds according to formula (I) contain one or more acidic or basic groups, the invention also comprises their corresponding pharmaceutically or toxicologically acceptable salts, in particular their pharmaceutically utilizable salts. Thus, the compounds of the formula (I), which contain acidic groups, can be present on these groups and can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Compounds of the formula (I), which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the compounds of the formula (I) simultaneously contain acidic and basic groups in the molecule, the invention also includes, in addition to the salt forms mentioned, inner salts or betaines (zwitterions). The respective salts according to the formula (I) can be obtained by customary methods, which are known to the person skilled in the art like, for example by contacting these with an organic or inorganic acid or base in a solvent or dispersant, or by anion exchange or cation exchange with other salts. The present invention also includes all salts of the compounds of the formula (I), which, owing to low physiological compatibility, are not directly suitable for use in pharmaceuticals but which can be used, for example, as intermediates for chemical reactions or for the preparation of pharmaceutically acceptable salts.

The present invention furthermore includes all solvates of compounds of the formula (I), for example hydrates or adducts with alcohols, active metabolites of the compounds of the formula (I), and also derivatives and prodrugs of the compounds of the formula (I) which contain physiologically tolerable and cleavable groups, for example esters, amides and compounds in which the N—H group depicted in formula (I) is replaced with an N-alkyl group, such as N-methyl, or with an N-acyl group, such as N-acetyl or N-argininyl, including pharmaceutically acceptable salts formed on functional groups present in the N-acyl group.

The compounds according to general formula (I) and their precursors can be prepared according to methods published in the literature or, respectively, analogous methods. Appropriate methods have been published in, for example, Houben-Weyl, Methoden der Organischen Chemie (Methods of Organic Chemistry), Thieme-Verlag, Stuttgart, or Organic Reactions, John Wiley & Sons, New York.

All reactions for the synthesis of the compounds of the formula (I) are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York. Depending on the circumstances of the individual case, in order to avoid side reactions during the synthesis of a compound of the formula (I), it can be necessary or advantageous to temporarily block functional groups by introducing protective groups and to deprotect them in a later stage of the synthesis, or introduce functional groups in the form of precursor groups which in a later reaction step are converted into the desired functional groups. Such synthesis strategies and protective groups and precursor groups, which are suitable in an individual case, are known to the skilled person. If desired, the compounds of the formula (I) can be purified by customary purification procedures, for example by recrystallization or chromatography. The starting compounds for the preparation of the compounds of the formula (I) are commercially available or can be prepared according to or analogously to literature procedures. The compounds obtained with the above-mentioned synthesis methods are a further object of the present invention.

The compounds according to the formula (I) can also be used in combination with other pharmaceutically active compounds, preferably compounds which are able to enhance the effect of the compounds according to the general formula (I). Examples of such compounds include: (i) antimetabolites, cytarabine, fludarabine, 5-fluoro-2'-deoxyuridine, gemcitabine, hydroxyurea or methotrexate; DNA-fragmenting agents, bleomycin, (iii) DNA-crosslinking and alkylating agents, chlorambucil, cisplatin, carboplatin, fotemustine, cyclophosphamide, ifosfamide, dacarbazine or nitrogen mustard; (iv) intercalating agents, adriamycin (doxorubicin) or mitoxantrone; (v) protein synthesis inhibitors, L-asparaginase, cycloheximide, puromycin or diphtheria toxin; (vi) topoisomerase I poisons, camptothecin or topotecan; (vii) topoisomerase II poisons, etoposide (VP-16) or teniposide; (viii) microtubule-directed agents, colcemid, colchicine, paclitaxel (taxol), docetaxel (taxotere), vinblastine or vincristine; (ix) kinase inhibitors, flavopiridol, staurosporin, ST1571 (CPG 57148B) or UCN-01 (7-hydroxystaurosporine); (x) miscellaneous investigational agents, trichostatin A, thioplatin, PS-341, phenylbutyrate, ET-18-OCH$_3$, or farnesyl transferase inhibitors (L-739749, L-744832); polyphenols, quercetin, resveratrol, piceatannol, epigallocatechine gallate, theaflavins, flavanols, procyanidins, betulinic acid and derivatives thereof; (xi) hormones, glucocorticoids or fenretinide; (xii) hormone antagonists, tamoxifen, finasteride or LHRH antagonists, (xiii) demethylating agents, 5-azacytidine, 5-aza-2' deoxycytidine, 5,6-dihydro-5-azacytidine, or (xiv) a combination of any of the pharmaceuticals given above or use in high-dose chemotherapy regimens including stem cell transplantation; (xv) differentiation inducing agents such as retinoic acid derivatives; (xvi) ionizing radiation therapy, MIBG-therapy and conventional radiation therapy.

The compounds of the formula (I) and their pharmaceutically acceptable salts, optionally in combination with other pharmaceutically active compounds, can be administered to animals, preferably to mammals, and in particular to humans, as pharmaceuticals by themselves, in mixtures with one another or in the form of pharmaceutical preparations. Further subjects of the present invention therefore also are the compounds of the formula (I) and their pharmaceutically acceptable salts for use as pharmaceuticals, including the use of the pharmaceuticals as inhibitor of centrosome clustering, to induce multipolar mitoses of tumor cells with supernumerary centrosomes, and to induce apoptosis. They can be used in the therapy and prophylaxis of the above-mentioned diseases and syndromes as well as for preparing pharmaceuticals for these purposes. Furthermore, subjects of the present invention are pharmaceutical preparations (or pharmaceutical compositions), which comprise an effective dose of at least one compound of the formula (I) and/or a pharmaceutically acceptable salt thereof and a pharmaceutically acceptable carrier, i.e. one or more pharmaceutically acceptable carrier substances and/or additives.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, for example, on the disease to be treated and on its severity.

The preparation of the pharmaceutical preparations can be carried out in a manner known per se. To this end, one or more compounds of the formula (I) and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form, which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Carriers for soft gelatin capsules and suppositories are, for example, fats, waxes, semisolid and liquid polyols, natural or hardened oils, etc. Suitable carriers for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formula (I) and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the compound or compounds according to the invention and carriers, the pharmaceutical preparations can also contain additives, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the compound of the formula (I) to be administered and/or of a pharmaceutically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to compounds of the formula (I). The daily dose can be administered in a single dose or, in particular when larger amounts are administered, be divided into several, for example two, three or four individual doses. In some cases, depending on the individual response, it may be necessary to deviate upwards or downwards from the given daily dose.

It is to be understood that the compounds identified in accordance with the method of the present invention may be used as pharmaceutical compositions to treat cancer and, preferably, even the cancer varieties referred to beforehand. Accordingly, the method of the present invention may further comprise the steps of manufacturing the identified compound as a pharmaceutical composition as described elsewhere in this specification.

The compounds 1 to 11 and P1 to P12 give representative examples of compounds, which have been prepared in the framework of the present invention, together with their activity, which has been determined as described below.

The invention will now be illustrated by the following Examples. However, the Examples are not meant to limit the scope of the invention in any respect.

Materials and Methods

Cell Culture. All cell lines were cultured in Dulbecco's modified Eagle's Medium (DMEM; PAA Laboratories, Pasching, Austria) supplemented with 10% FCS (PAA). SCC114 cells stably expressing GFP-α-tubulin were generated by transfection (Eugene 6, Roche Diagnostics, Mannheim, Germany) of the transgene in pEGFP-C1 (Clontech, Heidelberg, Germany) and maintained under selective pressure by addition of geniticin (Invitrogen, Karlsruhe, Germany) Primary normal human epidermal keratinocytes (NHEK; PromoCell, Heidelberg, Germany) were cultured in Keratinocyte Growth Medium 2 (PromoCell). When indicated a griseofulvin analogue was added to the culture medium. The griseofulvin analogue was dissolved in DMSO (Sigma). In all experiments, the final DMSO concentration was 0.1%.

Antibodies. The following antibodies were used: mouse monoclonal antibodies to Eg5 (Transduction Laboratories, Lexington, Ky.), α-tubulin (DM1A), γ-tubulin (GTU-88) (Sigma, Deisenhofen, Germany), δ-tubulin (A1), ε-tubulin (H280), PARP (F-2) (Santa Cruz, Heidelberg, Germany) dynein light intermediate chain (Chemicon International, Hampshire, UK), and NuMA (Calbiochem, Darmstadt, Germany); rabbit polyclonal antibodies to γ-tubulin, centrin (Sigma), pericentrin (Covance, Richmond, Calif.), actin (I-19) (Santa Cruz), and phospho-S10-histone H3 (Upstate Biotechnology, Lake Placid, N.Y.). A mouse monoclonal antibody to centrin and a rabbit polyclonal antibody to c-Nap I was kindly provided by J. L. Salisbury, Rochester, Min. and E. A. Nigg, Martinsried, Germany, respectively.

Immunofluorescence. Immunofluorescence staining was performed as described (Krämer et al., 2004). The following fluorochrome-conjugated secondary antibodies were used: anti-rabbit Alexa 488 (Molecular Probes, Invitrogen, Karlsruhe, Germany) and anti-mouse Cy3 (Jackson ImmunoResearch Laboratories, West Grove, Pa.). Immunostained cells were examined using a Zeiss Axiovert 200 M fluorescence microscope (Göttingen, Germany). Images were processed with Photoshop software (Adobe, Munich, Germany). [Krämer A, Mailand N, Lukas C, et al. Centrosome-associated Chk1 prevents premature activation of cyclin-B-Cdk1 kinase. Nat Cell Biol 2004; 6:884-891]

Time-lapse video microscopy. For live-cell imaging, GFP-α-tubulin expressing SCC114 cells were grown in $CO_2$-independent Leibovitz's medium (Gibco, Invitrogen, Karlsruhe, Germany) on plastic dishes (µ-dishes, Ibidi, Munich, Germany). Live-cell imaging was carried out using a Nikon TE2000-U inverted microscope equipped with differential interference contrast optics and an Orca AG camera (Hamamatsu), driven by NIS-Element AR software (Nikon). Individual GFP-α-tubulin expressing cells containing bipolar or multipolar spindles were detected by immunofluorescence and followed using differential interference contrast imaging.

Flow cytometry. Cell cycle analysis by flow cytometry including the quantification of cells in mitosis by phospho-S10-histone H3 staining was performed as previously described (Syljuasen et al., 2004)).

[Syljuasen R G, Sorensen C S, Nylandsted J, Lukas C, Lukas J, Bartek J. Inhibition of Chk1 by CEP-3891 accelerates mitotic nuclear fragmentation in response to ionizing Radiation. Cancer Res 2004; 64:9035-40]

Colorimetric MTT (tetrazolium) assay. The cytotoxicity assay was performed as previously described (Mosmann, 1983).

[Mosmann T. Rapid colorimetric assay for cellular growth and survival: application to proliferation and cytotoxicity assays. J Immunol Methods 1983; 65:55-63]

Isolation and analysis of human centrosomes. Centrosomes from SCC114 cells were isolated as previously described (Krämer et al., 2004; Blomberg-Wirschell and Doxsey, 1998).

[Krämer A, Mailand N, Lukas C, et al. Centrosome-associated Chk1 prevents premature activation of cyclin-B-Cdk1 kinase. Nat Cell Biol 2004; 6:884-891]

[Blomberg-Wirschell M, Doxsey S J. Rapid isolation of centrosomes. Methods Enzymol 1998; 298:228-38]

Measurement of Annexin-V-positive cells. Phosphatidylserine externalization was analyzed using the Apoptosis Detection Kit I from Becton Dickinson (Heidelberg, Germany) according to the manufacturer's recommendations.

Treatment of GFP-α-tubulin expressing SCC114 cells with griseofulvin analogues. Analogues were dissolved in DMSO/water and diluted to span a concentration range of 100 micromolar to 10 nanomolar.

Synthesis of griseofulvin derivatives. Griseofulvin and all other chemicals were purchased from Sigma-Aldrich and used without further purification. Thin-layer chromatography was performed on aluminum plates precoated with silica gel. Flash chromatography was performed using Merck silica gel 60. $^1$H NMR spectra were recorded on a Varian Unity Inova 500 spectrometer or a Varian Mercure 300 spectrometer and $^{13}$C NMR spectra on a Bruker AC 200 spectrometer operating at 50 MHz. IR spectra were obtained using a Perkin-Elmer 1600 FT-IR instrument. Melting points were determined using a Heidolph capillary melting point apparatus and are uncorrected. EIMS were recorded by direct inlet to a GCMS-QP5000 Gas Chromatograph Mass Spectrometer from Shimadzu. High-resolution LC-DAD-MS was performed on an Agilent 1100 system equipped with a photodiode array detector (DAD) and coupled to a LCT orthogonal time-of-flight mass spectrometer (Waters-Micromass, Manchester, UK) with a Z-spray electrospray ionisation (ESI) source and a LockSpray probe (M+H 556.2771) and controlled by MassLynx 4.0 software. LC-MS calibration from m/z 100-900 was done with a PEG mixture. Standard separation involved a LUNA 2 column with an acetonitrile (50 ppm TFA) in water gradient starting from 15% to 100% over 25 minutes with a flow rate of 0.3 mL/min. Microanalyses were conducted by H. Kolbe Mikroanalytisches Laboratorium, Mülheim an der Ruhr, Germany.

Synthesis of Representative, Active Compounds of the Formula (I):

General Procedure 1 for Compounds with Variation in Y, Z and $R^1$:

To a solution of 2'-demethoxy-2'-chloro griseofulvin (0.1 mmol, 1.0 equiv.) in dry THF (0.5 mL) was added a solution of a nucleophile (0.2 mmol, 2.0 equiv.) and NaH (0.3 mmol, 3.0 equiv.) in dry THF (0.25 mL). The mixture was stirred for 30 min and then quenched with $NH_4Cl$ (satd. aq.) and extracted with EtOAc (3×5 mL). The combined organic phases were dried with $MgSO_4$, concentrated in vacuo and purified by flash column chromatography. When possible the product was re-crystallized from EtOAc/heptane.

General Procedure 2 for Compounds with Variation in Y, Z, $R^1$ and $R^2$:

To an ice-cooled solution of griseofulvin (or 2'-analog) (1.4 mmol, 1 equiv.) and N-iodosuccinimide (2.1 mmol, 1.5 equiv.) in anhydrous $CH_2Cl_2$ (15 mL, 0.1 M) under an argon atmosphere was added triethylsilyl trifluoromethanesulfonate (0.35 mmol 0.25 equiv.). The mixture was stirred at 20° C. for 24 h and then diluted with $CH_2Cl_2$ (60 mL) and washed with sat. aq. $NaHCO_3$ (60 mL). The aqueous phase was extracted with $CH_2Cl_2$ (50 mL), the combined organic phases were dried ($MgSO_4$) and concentrated. The residue was purified by column chromatography (EtOAc:heptane 1:3) to yield the desired product. When possible the product was re-crystallized from EtOAc/heptane.

The following representative compounds were prepared according to general procedure 1:

(2S,6'R)-(7-Chloro-4,6-dimethoxy-benzofuran-3-one)-2-spiro-1'-(2'-(4-chlorobenzyloxy)-6'-methyl-cyclohex-2'-ene-4'-one) 1: $R_f$ (EtOAc:heptane 5:1): 0.42; m.p.: 173-175° C.; IR (KBr, cm$^{-1}$): 1705, 1659; $^1$H NMR (300 MHz, CDCl$_3$): δ 7.24 (2H, d, J=8.3 Hz), 7.09 (2H, d, J=8.3 Hz), 6.10 (1H, s), 5.54 (1H, s), 4.85 (1H, d, J=12.3 Hz), 4.73 (1H, d, J=12.3 Hz), 4.00 (3H, s), 3.94 (3H, s), 3.03 (1H, dd, J=16.5, 13.3 Hz), 2.84 (1H, ddq, J=13.3, 4.5, 6.6 Hz), 2.41 (1H, dd, J=16.5, 4.5 Hz), 0.96 (3H, d, J=6.6 Hz); $^{13}$C NMR (75 MHz, CDCl$_3$): δ 196.7, 192.6, 169.7, 169.6, 164.9, 158.0, 134.2, 133.4, 129.0 (2C), 128.3 (2C), 106.2, 105.3, 97.3, 90.3, 89.8, 70.1, 57.3, 56.6, 40.2, 36.6, 14.5; EIMS: m/e calcd for $C_{23}H_{20}Cl_2O_6$ M$^+$ 462. Found 462; Anal. Calcd for $C_{23}H_{20}Cl_2O_6$: C, 59.62; H, 4.35. Found: C, 59.68; H, 4.37.

(2S,6'R)-(7-Chloro-4,6-dimethoxy-benzofuran-3-one)-2-spiro-1'-(2'-(4-iodobenzyloxy)-6'-methyl-cyclohex-2'-ene-4'-one) 2: $R_f$ (EtOAc:heptane 5:1): 0.48; m.p.: 166-168° C.; IR (KBr, cm$^-$): 1702, 1657; $^1$H NMR (300 MHz, CDCl$_3$): δ 7.60 (2H, d, J=8.2 Hz), 6.90 (2H, d, J=8.2 Hz), 6.10 (1H, s), 5.54 (1H, s), 4.83 (1H, d, J=12.5 Hz), 4.71 (1H, d, J=12.5 Hz), 4.01 (3H, s), 3.95 (3H, s), 3.03 (1H, dd, J=16.5, 13.4 Hz), 2.90-2.78 (1H, m), 2.42 (1H, dd, J=16.5, 4.5 Hz), 0.96 (3H, d, J=6.6 Hz); $^{13}$C NMR (75 MHz, CDCl$_3$): δ 197.3, 192.6, 169.6, 164.9, 169.7, 153.0, 137.9 (2C), 134.5, 128.7 (2C), 106.2, 105.3, 97.4, 94.1, 90.9, 89.8, 70.2, 56.6, 57.3, 40.2, 36.6, 14.1; EIMS: m/e calcd for $C_{23}H_{20}ClIO_6$ M$^-$ 554. Found 554; Anal. Calcd for $C_{23}H_{20}ClIO_6$: C, 49.80; H, 3.63. Found: C, 49.89; H, 3.74.

(2S,6'R)-(7-Chloro-4,6-dimethoxy-benzofuran-3-one)-2-spiro-1'-(2'-(3-iodobenzyloxy)-6'-methyl-cyclohex-2'-ene-4'-one) 3: $R_f$ (EtOAc:heptane 5:1): 0.45; m.p.: 171-174° C.; IR (AgCl, cm$^{-1}$): 1704, 1660; $^1$H NMR (300 MHz, CDCl$_3$): δ 7.57 (1H, d, J=7.7 Hz), 7.42 (1H, s), 7.11 (1H, d, J=7.7 Hz), 7.00 (1H, t, J=7.8 Hz), 6.13 (1H, s), 5.55 (1H, s), 4.83 (1H, d, J=12.5 Hz), 4.71 (1H, d, J=12.5 Hz), 4.02 (3H, s), 3.97 (3H, s), 3.07 (1H, dd, J=16.5, 13.5 Hz), 2.93-2.80 (1H, m), 2.44 (1H, dd, J=16.5, 4.5 Hz), 0.99 (3H, d, J=6.6 Hz); $^{13}$C NMR (75 MHz, CDCl$_3$): δ 196.8, 192.7, 169.7, 169.5, 165.0, 158.0, 137.4, 137.2, 135.5, 130.5, 125.8, 106.1, 105.7, 97.1, 94.6, 91.0, 89.9, 69.5, 57.3, 56.7, 40.4, 36.5, 14.6; EIMS: m/e calcd for $C_{23}H_{20}ClIO_6$ M$^+$ 554. Found 554; Anal. Calcd for $C_{23}H_{20}ClIO_6$: C, 49.80; H, 3.63. Found: C, 49.69; H, 3.68.

(2S,6'R)-(7-Chloro-4,6-dimethoxy-benzofuran-3-one)-2-spiro-1'-(2'-(2-iodobenzyloxy)-6'-methyl-cyclohex-2'-ene- 4'-one) 4: R$_f$(EtOAc:heptane 5:1): 0.48; m.p.: 167-169° C.; IR (AgCl, cm$^{-1}$): 1706, 1661; $^1$H NMR (300 MHz, CDCl$_3$): δ 7.60-754 (1H, m), 7.45-7.41 (1H, m), 7.19-7.09 (1H, m), 7.05-6.97 (1H, m), 6.12 (1H, s), 5.63 (1H, s), 4.85 (1H, d, J=13.3 Hz), 4.71 (1H, d, J=13.2 Hz), 4.03 (3H, s), 3.97 (3H, s), 3.08 (1H, dd, J=16.5, 13.4 Hz), 2.95-2.83 (1H, m), 2.46 (1H, dd, J=16.5, 4.4 Hz), 1.00 (3H, d, J=6.6 Hz); $^{11}$C NMR (75 MHz, CDCl$_3$): δ 196.9, 192.6, 169.8, 169.4, 164.9, 158.1, 139.5, 137.0, 130.0, 128.6, 128.1, 106.4, 105.2, 97.1, 96.5, 91.0, 89.8, 74.7, 57.3, 56.7, 40.3, 36.7, 14.5; EIMS: m/e calcd for C$_{23}$H$_{20}$ClIO$_6$ M$^+$ 554. Found 554.

(2S,6'R)-(7-Chloro-4,6-dimethoxy-benzofuran-3-one)-2-spiro-1'-(6'-methyl-2'-(4-methylbenzyloxy)-cyclohex-2'-ene-4'-one) 5: R$_f$(EtOAc:heptane 5:1): 0.45; m.p.: 176-178° C.; IR (KBr, cm$^{-1}$): 1709, 1664; $^1$H NMR (300 MHz, CDCl$_3$): δ 7.11-7.04 (4H, m), 6.09 (1H, s), 5.58 (1H, s), 4.87 (1H, d, J=12.2 Hz), 4.76 (1H, d, J=12.2 Hz), 4.01 (3H, s), 3.95 (3H, s), 3.04 (1H, dd, J=16.5, 13.4 Hz), 2.85 (1H, ddq, J=13.2, 4.5, 6.6 Hz), 2.41 (1H, dd, J=16.4, 4.4 Hz), 2.30 (3H, s), 0.97 (3H, d, J=6.6 Hz); $^{13}$C NMR (75 MHz, CDCl$_3$): δ 197.1, 192.7, 169.9, 169.8, 164.7, 157.9, 138.2, 131.8, 129.5 (2C), 127.0 (2C), 106.2, 105.8, 97.1, 91.0, 89.7, 71.0, 57.2, 56.6, 40.2, 36.7, 21.4, 14.5; HRMS (ESI+) calcd for [C$_{24}$H$_{24}$ClO$_6$] 443.1261, found 443.1273.

(2S,6'R)-(7-Chloro-4,6-dimethoxy-benzofuran-3-one)-2-spiro-1'-(6'-methyl-2'-(4-hydroxymethylbenzyloxy)-cyclohex-2'-ene-4'-one) 6: $^1$H NMR (300 MHz, CDCl$_3$): δ 7.31 (d, J=8.3 Hz, 2H), 7.14 (d, J=8.3 Hz, 2H), 6.11 (s, 1H), 5.56 (s, 1H), 4.90 (d, J=12.5 Hz, 1H), 4.79 (d, J=12.5 Hz, 1H), 4.44 (s, 2H), 4.02 (s, 3H), 3.96 (s, 3H), 3.04 (dd, J=16.5, 13.4 Hz, 1H), 2.86 (ddq, J=13.4, 4.5, 6.6 Hz, 1H), 2.42 (dd, J=16.5, 4.5 Hz, 1H), 0.98 (d, J=6.6 Hz, 3H).

(2S,6'R)-(7-Chloro-4,6-dimethoxy-benzofuran-3-one)-2-spiro-1'-(6'-methyl-2'-(4-bromo-methylbenzyloxy)-cyclohex-2'-ene-4'-one) 7: $^1$H NMR (300 MHz, CDCl$_3$): δ 7.31 (d, J=8.1 Hz, 2H), 7.14 (d, J=8.1 Hz, 2H), 6.10 (s, 1H), 5.56 (s, 1H), 4.90 (d, J=12.5 Hz, 1H), 4.78 (d, J=12.5 Hz, 1H), 4.44 (s, 2H), 4.02 (s, 3H), 3.96 (s, 3H), 3.04 (dd, J=16.5, 13.5 Hz, 1H), 2.85-2.76 (m, 1H), 2.42 (dd, J=16.5, 4.4 Hz, 1H), 0.97 (d, J=6.6 Hz, 3H).

(2S,6'R)-(7-Chloro-4,6-dimethoxy-benzofuran-3-one)-2-spiro-1'-(6'-methyl-2'-((3,5-dimethyl-4-nitro-pyrid-2-yl)methyloxy)-cyclohex-2'-ene-4'-one) 8: $^1$H NMR (300 MHz, CDCl$_3$): δ 7.35 (s, 1H), 6.10 (s, 1H), 5.75 (s, 1H), 5.03 (s, 2H), 4.00 (s, 3H), 3.95 (s, 3H), 3.01 (dd, J=16.5, 13.5 Hz, 1H), 2.80 (ddq, J=13.5, 4.5, 6.7 Hz, 1H), 2.39 (dd, J=16.5, 4.4 Hz, 1H), 2.25 (s, 3H), 2.12 (s, 3H) 0.93 (d, J=6.7 Hz, 3H).

(2S,6'R)-(7-Chloro-4,6-dimethoxy-benzofuran-3-one)-2-spiro-1'-(2'-(4-biphenylmethoxy)-6'-methyl-cyclohex-2'-ene-4'-one) 9: R$_f$ (toluene:CH$_2$Cl$_2$:heptane 2:2:1); 0.32; IR (KBr, cm$^{-1}$): 1704, 1662; $^1$H-NMR (300 MHz, CDCl$_3$): δ 7.58-7.50 (4H, m), 7.46-7.40 (2H, m), 7.37-7.31 (1H, m), 7.28-7.23 (2H, m), 6.10 (1H, s), 5.63 (1H, s), 4.97 (1H, d, J=12.4 Hz), 4.85 (1H, d, J=12.4 Hz), 4.01 (3H, s), 3.96 (3H, s), 3.07 (1H, dd, J=16.5, 13.4 Hz), 2.88 (1H, ddq, J=13.4, 4.6, 6.6 Hz), 2.45 (1H, dd, J=16.5, 4.6 Hz), 1.00 (3H, d, J=6.6 Hz); $^{13}$C NMR (50 MHz, CDCl$_3$); 197.0, 192.4, 169.5 (2C), 164.5, 157.7, 141.0, 140.4, 133.6, 128.7 (4C), 127.2, 127.0 (4C), 105.9, 105.3, 97.2, 90.7, 89.4, 70.4, 56.9, 56.3, 40.0, 36.3, 14.2; HRMS (ESI+) calcd for [C$_{29}$H$_{26}$ClO$_6$]$^+$ 505.1418, found 505.1421.

(2S,6'R)-(7-Chloro-4,6-dimethoxy-benzofuran-3-one)-2-spiro-1'-(6'-methyl-2'-phenoxy-cyclohex-2'-ene-4'-one) 10: R$_f$ (EtOAc:heptane 5:1): 0.50; IR (KBr, cm$^{-1}$): 1704, 1665; $^1$H NMR (300 MHz, CDCl$_3$): δ 7.36-7.29 (2H, m), 7.22-7.16 (1H, m), 7.00-6.95 (2H, m), 6.13 (1H, s), 5.30 (1H, s), 4.01 (3H, s), 3.99 (3H, s) 3.06 (1H, dd, J=16.0, 13.5 Hz), 2.99-2.85 (1H, m), 2.42 (1H, dd, J=16.0, 4.0 Hz), 1.01 (3H, d, J=6.5 Hz); $^{13}$C NMR (75 MHz, CDCl$_3$); 197.0, 192.3, 170.9, 169.6, 164.8, 157.8, 152.6, 130.0 (2C), 126.3, 121.1 (2C), 108.8, 105.2, 97.2, 90.6, 89.5, 57.0, 56.4, 40.3, 36.5, 14.3; HRMS (ESI+) calcd for [C$_{22}$H$_{20}$ClO$_6$]$^+$ 415.0948, found 415.0941.

The following representative compound was prepared according to general procedure 2:

(2S,6'R)-(7-Chloro-4,6-dimethoxy-benzofuran-3-one)-2-spiro-1'-(3'-iodo-6'-methyl-2'-propoxy-cyclohex-2'-ene-4'-one) 11: R$_f$(EtOAc:heptane 5:1): 0.53; m.p.: 98-100° C.; IR (KBr, cm$^{-1}$): 1719, 1618; $^1$H NMR (500 MHz, CDCl$_3$): δ 6.13 (1H, s), 4.14-4.11 (2H, m), 4.03 (3H, s), 4.00 (3H, s), 3.80-3.73 (1H, m), 2.94-2.87 (1H, m), 2.92-2.90 (1H, m), 1.75-1.68 (2H, m), 1.05 (3H, d, J=5.8 Hz), 1.00 (3H, t, J=7.4 Hz); $^{13}$C NMR (75 MHz, CDCl$_3$): δ 196.7, 192.1, 188.0, 172.3, 172.3, 165.5, 158.3, 112.2, 103.8, 97.9, 90.1, 67.9, 57.4, 56.8, 39.4, 38.2, 22.3, 12.2, 10.8; HRMS (ESI+) calcd for [C$_{19}$H$_{21}$ClO$_6$]$^+$ 507.0071, found 507.0069.

The IC$_{50}$ values for the compounds 1 to 11 are shown in table 1

TABLE 1

| Compound | IC$_{50}$ [μM] |
|---|---|
| 1 | 3.4 |
| 2 | 3.3 |
| 3 | * |
| 4 | 5.8 |
| 5 | 0.9 |
| 6 | 1.2 |
| 7 | 4.7 |
| 8 | 9.1 |
| 9 | 3.2 |
| 10 | 1.5 |
| 11 | 2.1 |

* Compound 3 is expected to show IC$_{50}$ values in the range from 0.1 to 10 μM.

The structure of the compounds 1 to 11 is shown below:

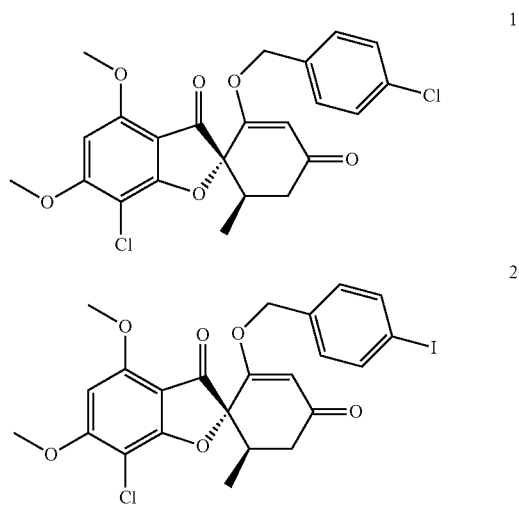

3
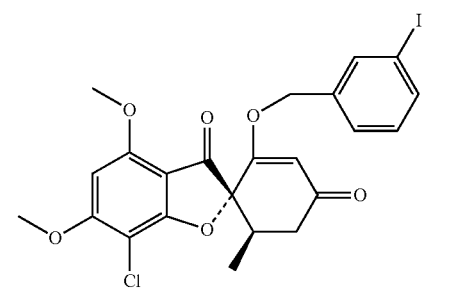
4
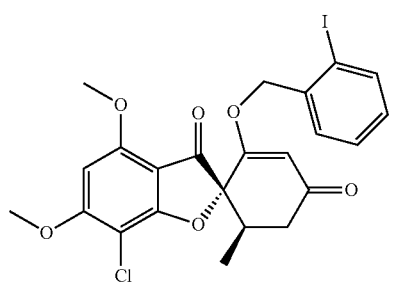
5
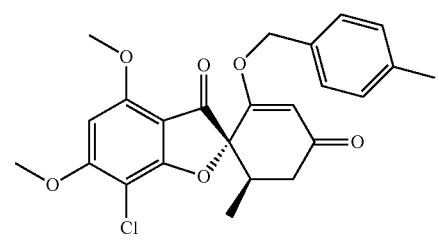
6
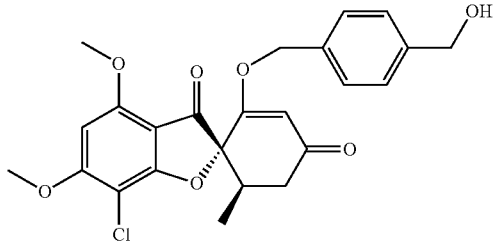
7
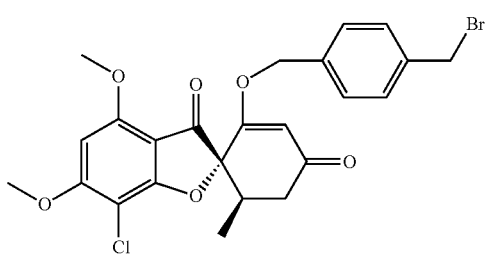
8
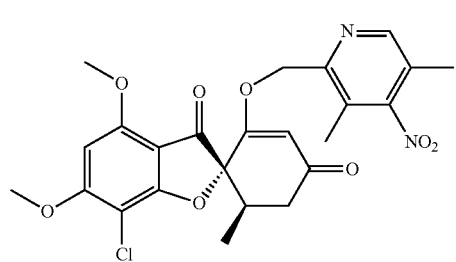
9
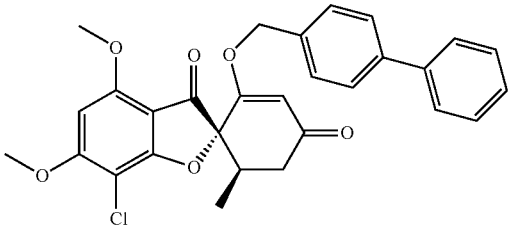
10
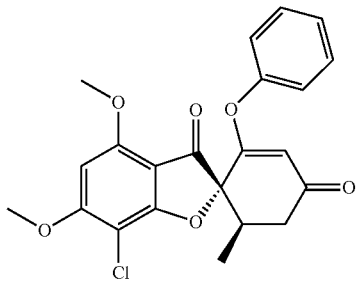
11
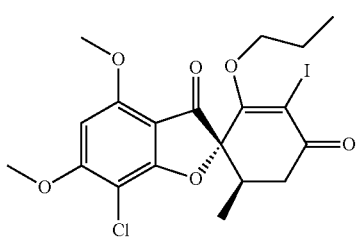
It is expected, that the following compounds P1 to P12 can be synthesised in a straight-forward manner.
P1
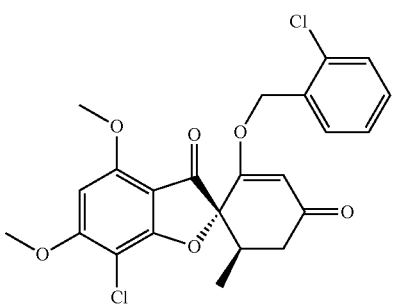
P2
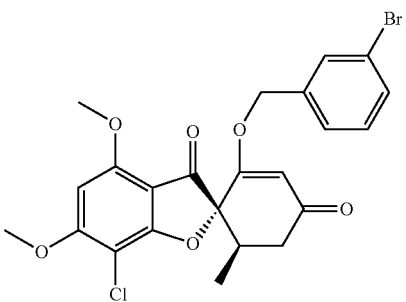

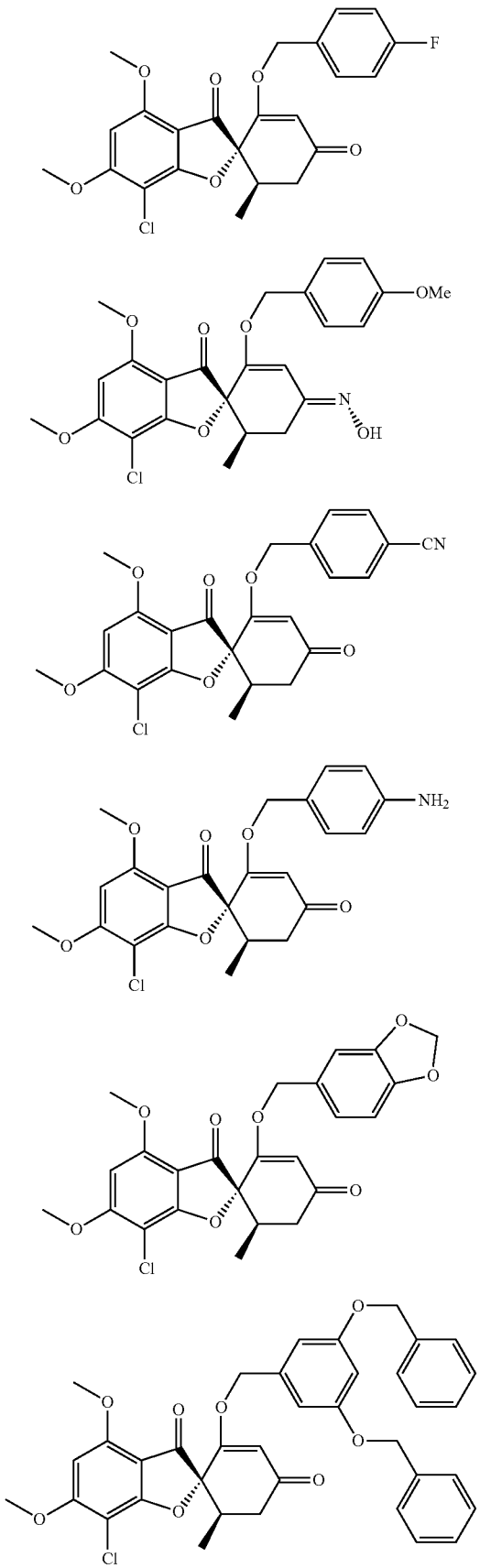
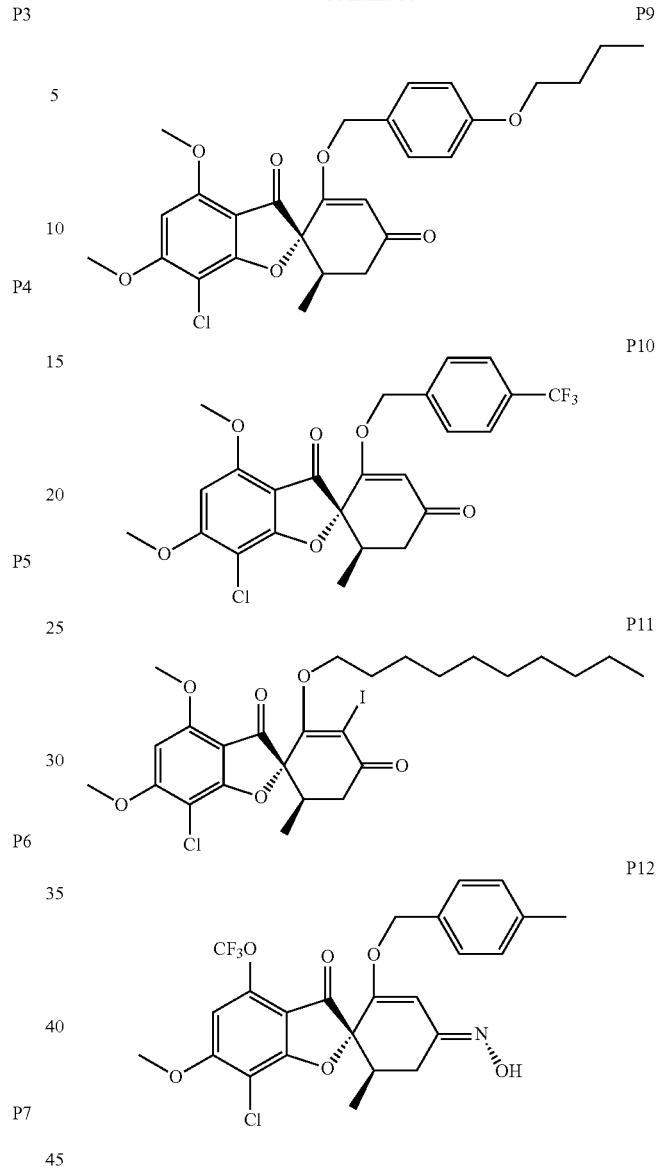

The IUPAC names of the compounds P1 to P12 are as follows:

(2S,6'R)-(7-Chloro-4,6-dimethoxy-benzofuran-3-one)-2-spiro-1'-(2'-(2-chlorobenzyloxy)-6'-methyl-cyclohex-2'-ene-4'-one) P1.

(2S,6'R)-(7-Chloro-4,6-dimethoxy-benzofuran-3-one)-2-spiro-1-bromobenzyloxy)-6'-methyl-cyclohex-2'-ene-4'-one) P2.

(2S,6'R)-(7-Chloro-4,6-dimethoxy-benzofuran-3-one)-2-spiro-1'-(2'-(4-fluorobenzyloxy)-6'-methyl-cyclohex-2'-ene-4'-one) P3.

(2S,6'R)-(7-Chloro-4,6-dimethoxy-benzofuran-3-one)-2-spiro-1'-(2'-(4-methoxybenzyloxy)-6'-methyl-cyclohex-2'-ene-4'-one-4'-oxime) P4.

(2S,6'R)-(7-Chloro-4,6-dimethoxy-benzofuran-3-one)-2-spiro-1'-(2'-(4-cyanobenzyloxy)-6'-methyl-cyclohex-2'-ene-4'-one) P5.

(2S,6'R)-(7-Chloro-4,6-dimethoxy-benzofuran-3-one)-2-spiro-1'-(2'-(4-aminobenzyloxy)-6'-methyl-cyclohex-2'-ene-4'-one) P6.

(2S,6'R)-(7-Chloro-4,6-dimethoxy-benzofuran-3-one)-2-spiro-1'-(2'-(benzo[1,3]dioxol-5-ylmethoxy)-6'-methyl-cyclohex-2'-ene-4'-one) P7.

(2S,6'R)-(7-Chloro-4,6-dimethoxy-benzofuran-3-one)-2-spiro-1'-(2'-(3,5-dibenzyloxybenzyloxy)-6'-methyl-cyclohex-2'-ene-4'-one) P8.

(2S,6'R)-(7-Chloro-4,6-dimethoxy-benzofuran-3-one)-2-spiro-1'-(2'-(4-butyloxybenzyloxy)-6'-methyl-cyclohex-2'-ene-4'-one) P9.

(2S,6'R)-(7-Chloro-4,6-dimethoxy-benzofuran-3-one)-2-spiro-1'-(2'-(4-trifluoromethylbenzyloxy)-6'-methyl-cyclohex-2'-ene-4'-one) P10.

(2S,6'R)-(7-Chloro-4,6-dimethoxy-benzofuran-3-one)-2-spiro-1'-(2'-decyloxy-3'-iodo-6'-methyl-cyclohex-2'-ene-4'-one) P11.

(2S,6'R)-(7-Chloro-4-trifluoromethoxy-6-methoxy-benzofuran-3-one)-2-spiro-1'-(2'-(4-methylbenzyloxy)-6'-methyl-cyclohex-2'-ene-4'-one-4'-oxime) P12.

The expected $IC_{50}$ values of the compounds P1 to P12 are shown in table 2.

TABLE 2

| Compound | $IC_{50}$ [μM] |
| --- | --- |
| P1 | 0.1-3 |
| P2 | 0.1-2 |
| P3 | 0.1-1 |
| P4 | 0.1-0.5 |
| P5 | 0.1-0.7 |
| P6 | 0.1-5 |
| P7 | 0.01-0.2 |
| P8 | 1-15 |
| P9 | 0.001-0.1 |
| P10 | 0.01-0.5 |
| P11 | 1-8 |
| P12 | 0.001-0.05 |

The invention claimed is:

1. A compound of the formula (I)

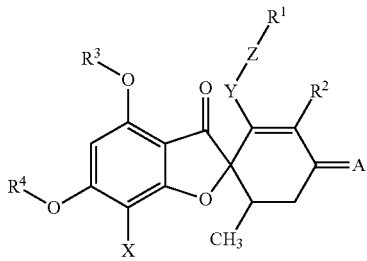

(I)

wherein the symbols in formula (I) have the following meanings:

A is =O,
X is Cl,
Y is —O—,
Z is —(CH$_2$)$_n$—,
n is 0 or 1,
$R^2$ is hydrogen or halogen,
$R^1$ is, in case $R^2$ is hydrogen and n is other than 0: phenyl or pyridyl, wherein the phenyl, or pyridyl group is substituted on one or more ring carbon atoms by identical or different substituents $R^{10}$,
$R^1$ is, in case $R^2$ is hydrogen and n is 0: phenyl, wherein the phenyl group is substituted on one or more ring carbon atoms by identical or different substituents $R^{10}$,
$R^1$ is, in case $R^2$ is halogen: linear or branched (C$_1$-C$_{10}$)-alkyl,
$R^{10}$ is halogen, nitro, linear or branched (C$_1$-C$_{10}$)-alkyl, phenyl hydroxyl-(C$_1$-C$_4$)-alkyl, or halogen-(C$_1$-C$_4$)-alkyl,
$R^3$ is methyl,
$R^4$ is methyl,
and/or a pharmaceutically acceptable salt thereof.

2. A pharmaceutical composition for the treatment of colon cancer, lung cancer, melanoma, leukemia, or ovarian cancer, comprising a therapeutically effective amount of a compound as claimed in claim 1 and optionally carriers and additives.

3. A method for treating colon cancer, lung cancer, melanoma, leukemia, or ovarian cancer in a patient, comprising administering to a patient suffering from said cancer, in a therapeutically effective amount a compound according to the general formula (I) and/or a pharmaceutically acceptable salt thereof,

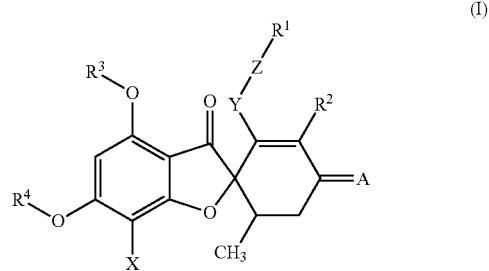

(I)

wherein the symbols in formula (I) have the following meanings:

A is =O,
X is Cl,
Y is —O—,
Z is —(CH$_2$)$_n$—,
n is 0 or 1,
$R^2$ is hydrogen or halogen,
$R^1$ is, in case $R^2$ is hydrogen and n is other than 0: phenyl, or pyridyl, wherein the phenyl, or pyridyl group is substituted on one or more ring carbon atoms by identical or different substituents $R^{10}$,
$R^1$ is, in case $R^2$ is hydrogen and n is 0: phenyl, wherein the phenyl group is unsubstituted or substituted on one or more ring carbon atoms by identical or different substituents $R^{10}$,
$R^1$ is, in case $R^2$ is halogen: linear or branched (C$_1$-C$_{10}$)-alkyl,
$R^{10}$ is halogen, nitro, linear or branched (C$_1$-C$_{10}$)-alkyl, phenyl hydroxyl-(C$_1$-C$_4$)-alkyl, or halogen-(C$_1$-C$_4$)-alkyl,
$R^3$ is methyl,
$R^4$ is methyl,
and/or a pharmaceutically acceptable salt thereof.

4. A method for the inhibition of centrosome clustering in a tumor cell comprising contacting the tumor cell with a compound according to formula (I);

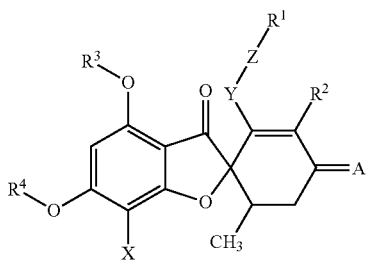

wherein the symbols in formula (I) have the following meanings:
A is =O,
X is Cl,
Y is —O—,
Z is —(CH$_2$)$_n$—,
n is or 0 or 1,
R$^2$ is hydrogen or halogen,
R$^1$ is, in case R$^2$ is hydrogen and n is other than 0: phenyl, or pyridyl, wherein the phenyl, or pyridyl group is substituted on one or more ring carbon atoms by identical or different substituents R$^{10}$,
R$^1$ is, in case R$^2$ is hydrogen and n is 0: phenyl, wherein the phenyl group is unsubstituted or substituted on one or more ring carbon atoms by identical or different substituents R$^{10}$,
R$^1$ is, in case R$^2$ is halogen: linear or branched (C$_1$-C$_{10}$)-alkyl,
R$^{10}$ s halogen, nitro, linear or branched (C$_1$-C$_{10}$)-alkyl, phenyl hydroxyl-(C$_1$-C$_4$)-alkyl, or halogen-(C$_1$-C$_4$)-alkyl,
R$^3$ is methyl,
R$^4$ is methyl,
and/or a pharmaceutically acceptable salt thereof.

5. The method of claim 4, wherein said tumor cell is in a patient with colon cancer, lung cancer, melanoma, leukemia, or ovarian cancer.

6. A method to induce multipolar mitoses in a tumor cell with supernumerary centrosomes comprising contacting the tumor cell with a compound according to formula (I);

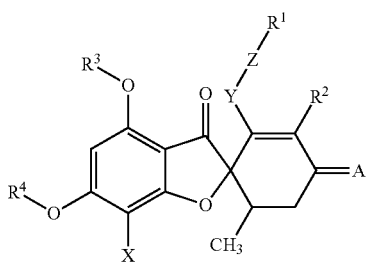

wherein the symbols in formula (I) have the following meanings:
A is =O,
X is Cl,
Y is —O—,
Z is —(CH$_2$)$_n$—,
n is 0 or 1,
R$^2$ is hydrogen or halogen,
R$^1$ is, in case R$^2$ is hydrogen and n is other than 0: phenyl or pyridyl, wherein the phenyl, or pyridyl group is substituted on one or more ring carbon atoms by identical or different substituents R$^{10}$,
R$^1$ is, in case R$^2$ is hydrogen and n is 0: phenyl, wherein the phenyl group is unsubstituted or substituted on one or more ring carbon atoms by identical or different substituents R$^{10}$,
R$^1$ is, in case R$^2$ is halogen: linear or branched (C$_1$-C$_{10}$)-alkyl,
R$^{10}$ is halogen, nitro, linear or branched (C$_1$-C$_{10}$)-alkyl, phenyl hydroxyl-(C$_1$-C$_4$)-alkyl, or halogen-(C$_1$-C$_4$)-alkyl,
R$^3$ is methyl or,
R$^4$ is methyl,
and/or a pharmaceutically acceptable salt thereof.

7. The method of claim 6, wherein said tumor cell is in a patient with colon cancer, lung cancer, melanoma, leukemia, or ovarian cancer.

8. A method to induce apoptosis in a tumor cell, comprising contacting the tumor cell with a compound according to formula (I);

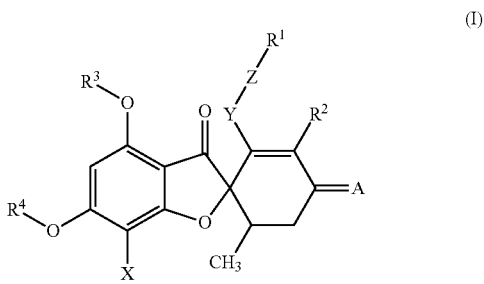

wherein the symbols in formula (I) have the following meanings:
A is =O,
X is Cl,
Y is —O—,
Z is —(CH$_2$)$_n$—,
n is 0 or 1,
R$^2$ is hydrogen or halogen,
R$^1$ is, in case R$^2$ is hydrogen and n is other than 0: phenyl, or pyridyl, wherein the phenyl, or pyridyl group is substituted on one or more ring carbon atoms by identical or different substituents R$^{10}$,
R$^1$ is, in case R$^2$ is hydrogen and n is 0: phenyl, wherein the phenyl group is unsubstituted or substituted on one or more ring carbon atoms by identical or different substituents R$^{10}$, R$^1$ is, in case R$^2$ is halogen: linear or branched (C$_1$-C$_{10}$)alkyl,
R$^{10}$ is halogen, nitro, linear or branched (C$_1$-C$_{10}$)-alkyl, phenyl, hydroxyl-(C$_1$-C$_4$)-alkyl, or halogen-(C$_1$-C$_4$)-alkyl,
R$^3$ is methyl or,
R$^4$ is methyl,
and/or a pharmaceutically acceptable salt thereof.

9. The method of claim 8, wherein said tumor cell is in a patient with colon cancer, lung cancer, melanoma, leukemia, or ovarian cancer.

* * * * *